United States Patent
Mandrake et al.

(10) Patent No.: US 10,451,570 B2
(45) Date of Patent: Oct. 22, 2019

(54) BACKSCATTER IMAGING SYSTEMS AND METHODS WITH HELICAL MOTION

(71) Applicant: California Institute of Technology, Pasadena, CA (US)

(72) Inventors: Lukas Mandrake, Altadena, CA (US); Martin W. Lo, Altadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 235 days.

(21) Appl. No.: 15/585,026

(22) Filed: May 2, 2017

(65) Prior Publication Data
US 2017/0315067 A1  Nov. 2, 2017

Related U.S. Application Data

(60) Provisional application No. 62/330,437, filed on May 2, 2016.

(51) Int. Cl.
*G01N 23/203* (2006.01)

(52) U.S. Cl.
CPC ..... *G01N 23/203* (2013.01); *G01N 2223/053* (2013.01); *G01N 2223/1003* (2013.01); *G01N 2223/315* (2013.01)

(58) Field of Classification Search
CPC .......... G01N 2223/315; G01N 23/203; G01N 2223/1003; G01N 2223/053; A61B 6/483
See application file for complete search history.

(56) References Cited

U.S. PATENT DOCUMENTS

| | | | |
|---|---|---|---|
| 5,430,787 A | 7/1995 | Norton | |
| 6,556,653 B2 | 4/2003 | Hussein | |
| 6,563,906 B2 | 5/2003 | Hussein et al. | |
| 7,203,276 B2 | 4/2007 | Arsenault et al. | |
| 7,634,059 B2 | 12/2009 | Wraight | |
| 7,960,687 B1 | 6/2011 | Simon et al. | |
| 8,705,694 B2 | 4/2014 | Grubsky et al. | |
| 2007/0172026 A1* | 7/2007 | Schlomka | A61B 6/032 378/19 |
| 2011/0122994 A1 | 5/2011 | Grubsky et al. | |

(Continued)

FOREIGN PATENT DOCUMENTS

| | | |
|---|---|---|
| WO | WO 2008/069674 A1 | 6/2008 |
| WO | WO 2011/059545 A2 | 5/2011 |
| WO | WO 2012/050725 A2 | 4/2012 |

OTHER PUBLICATIONS

Als-Nielsen, J. et al., "Elements of Modern X-ray Physics," Second Edition, Wiley, pp. 1-419, (2011). [ISBN 978-0-470-97394-3].

(Continued)

*Primary Examiner* — Chih-Cheng Kao
(74) *Attorney, Agent, or Firm* — Sheila Martinez-Lemke; Weaver Austin Villeneuve & Sampson LLP

(57) ABSTRACT

Backscatter imaging systems and methods that involve moving an emitter and a broad spectrum detector in helical motion along a medium being imaged while the emitter emits substantially monochromatic X-rays and/or gamma rays, and the broad spectrum detector acquires intensity measurement of photons backscattered from the medium. The intensity measurements are transformed into three-dimensional image data of the medium corresponding to density variations.

21 Claims, 8 Drawing Sheets

A1-A1'

(56) References Cited

U.S. PATENT DOCUMENTS

| | | | |
|---|---|---|---|
| 2013/0206985 A1 | 8/2013 | Turner et al. | |
| 2015/0377804 A1* | 12/2015 | Arsenault | G01N 23/20066 |
| | | | 250/393 |
| 2016/0033426 A1 | 2/2016 | Georgeson et al. | |
| 2016/0187528 A1 | 6/2016 | Sofiienko et al. | |
| 2017/0052125 A1 | 2/2017 | Georgeson et al. | |

OTHER PUBLICATIONS

Arendtsz et al., "Electron Density Tomography with Compton Scattered Radiation," Proc. SPIE vol. 2035, Mathematical Methods in Medical Imaging II, Jun. 23, 1993, pp. 230-241. [retrieved Oct. 16, 2013] <URL: http://proceedings.spiedigitallibrary.org>.

Arsenault, J. PhD., "Backscatter Computed Tomography Development Overview," Inversa Systems, Nov. 1, 2012, pp. 1-15. <URL:http://www.inversasystems.com>.

Arsenault, J. PhD., et al., "X-Ray Scatter Image Reconstruction by Balancing Discrepancies Between Detector Responses," PhD Thesis, University of New Brunswick, Oct. 2004, pp. 1-194. [ISBN: 978-0-494-46752-7].

Arsenault, J., and Hussein, E., "Image Reconstruction From the Compton Scattering of X-Ray Fan Beams in Thick/Dense Objects," IEEE Transactions on Nuclear Science, vol. 53, No. 3, Jun. 2006, pp. 1622-1633.

Callerame, J. (2006) "X-Ray Backscatter Imaging: Photography Through Barriers", JCPDS—International Center for Diffraction Data (2006), pp. 13-20. [ISSN 1097-0002].

Chen, P. & Y. Wang (1996) "Multicriterion Compton Backscatter Imaging", IEE Proc.-Sci. Meas. Technol., vol. 143, No. 6, Nov. 1996, pp. 357-361. <doi: 10.1049/ip-smt:19960279>.

El Khettabi, F. et al., "An Inverse Problem for Three-Dimensional X-Ray Scatter/Transmission Imaging," Inverse Problems, vol. 19, No. 2, Mar. 14, 2003, pp. 477-495. <URL:https://doi.org/10.1088/0266-5611/19/2/314>.

EM&I StantecLtd., "EM&I Stantec and Inversa Systems pioneer unique new technical solutions," Stantec Media Relations (Press Release) posted May 28, 2012, pp. 2. <URL:www.inversasystems.com>.

Harding, G., et al., "Compton scatter imaging: A tool for historical exploration", Applied Radiation and Isotopes, vol. 68, No. 6, Jun. 2010, pp. 993-1005. <doi:10.1016/j.apradiso.2010.01.035>.

Hussein, M.A., "The physical and mathematical aspects of inverse problems in radiation detection and applications," Applied Radiation and Isotopes, vol. 70, No. 7, Jul. 2012, pp. 1131-1135. <doi:10.1016/j.apradiso.2011.11.041>.

Kittmer, C.A., "Fifth Pan Pacific Conference on Nondestructive Testing," Proceedings/Notes De La Conference, Apr. 1987, Vancouver, CA., Atomic Energy of Canada Limited (AECL-9394) pp. 1-604. <ISSN: 0067-0367>.

Kondic, N. N., "Density field determination by an external stationary radiation source using a kernel technique," Measurements in polyphase flows Symposium, ASME Winter Annual Meeting, D. E. Stock Ed., 3751 ASME, 978-9-99376-428-1, Dec. 10-15, 1978, pp. 1-18.

Marmier, P. et al., Chapter 4.2 "Thomson and Compton Scattering of Gamma-Radiation," Physics of Nuclei and Particles vol. I, Academic Press Inc., New York (1969), pp. 103-111. [OSTI ID:4783016].

Truong, T.T., et al., "Recent Developments on Compton Scatter Tomography: Theory and Numerical Simulations," INTECH, Numerical Simulation-From Theory to Industry, Chapter 6., Sep. 19, 2012, pp. 101-128. <doi:10.5772/50012> [retrieved Apr. 7, 2017] <URL:https://dx.doi.org/10.5772/50012>.

"WrapSight™—Temporary Repair Inspection & Management," EM&I Ltd., 2016 WrapSight Leaflet Ex DM, pp. 2. [retrieved on Apr. 19, 2017] <URL:http://www.emialliance.com>.

Cormack, A. M., "Representation of a Function by Its Line Integrals, with Some Radiological Applications," J. Appl. Phys., vol. 34, No. 9, Sep. 1963, pp. 2722-2727. <URL:https://doi.org/10.1063/1.172978>.

Cormack, A. M., "The Radon Transform on a Family of Curves in the Plane, II," Proceedings of the American Mathematical Society, vol. 86, No. 2, Oct. 1982, pp. 293-298.

PCT International Search Report and Written Opinion of the International Searching Authority dated, May 10, 2018, for International Patent Application PCT/US2017/059599, 15 pages.

Cormack, A. M., "The Radon transform on a family of curves in the plane," Proceedings of the American Mathematical Society, vol. 83, No. 2, Oct. 1981, pp. 325-330.

* cited by examiner

A - A'

A1-A1'

*B - B'*

A-A'

BACKSCATTER IMAGING SYSTEMS AND METHODS WITH HELICAL MOTION

CROSS-REFERENCE TO RELATED APPLICATION

This application claims benefit under 35 U.S.C. § 119(e) to U.S. Provisional Patent Application No. 62/330,437, titled "Design of X-Ray Backscatter Imager Using Generalized RADON Transforms for Oil Well Integrity Verification" and filed May 2, 2016, which is hereby incorporated by reference in its entirety and for all purposes.

FEDERALLY SPONSORED RESEARCH OR DEVELOPMENT

The invention described herein was made in the performance of work under a NASA contract NNN12AA01C, and is subject to the provisions of Public Law 96-517 (35 USC 202) in which the Contractor has elected to retain title.

FIELD

Certain embodiments described herein are generally related to imaging techniques, and more particularly, to backscatter-based imaging techniques for three-dimensional imaging that can be implemented, for example, in non-destructive inspection and identification of material composition and structure such as could be used in inspecting the integrity of an oil well wall and mineralogical identification of surrounding rock formations.

BACKGROUND

Imaging deep into bodies using high energy radiation is ubiquitous in planetary exploration, oil well investigation, baggage scanning, border security, and many other applications. Gamma rays are highly penetrative, but irradiate and activate the target materials. While X-rays offer a safer alternative, conventional designs typically suffer from low signal-to-noise detection and require the detector and emitter to be located on opposite sides of the target being imaged and comprehensively rotated around the object to be imaged. This two-sided geometry is difficult, if not impossible, to achieve in many applications such as when imaging into a large, extended volume or through a highly absorptive/scattering medium. Although back-scattering of X-rays can be used for one-sided imaging where the X-ray source and detector are located on the same side of the medium with a significantly reduced signal-to-noise solution, current backscatter imaging schemes tend to be large, mechanically complex, and require assumptions on the medium to be imaged such as low X-ray absorptivity. Small volume requirements on spacecraft or within oil shafts prevent use of the typical 2D sensor grid required for high-fidelity X-ray imaging. Extreme temperatures and pressures such as within an oil shaft, at the bottom of the ocean, or on planets like Venus require extensive protective casings that further reduce available volume and force X-rays to first traverse the casing before reaching the target medium.

SUMMARY

Certain aspects pertain to a backscatter imaging system for three-dimensional imaging of a medium. In these aspects, the backscatter imaging system comprises an emitter configured to provide substantially monochromatic radiation and a broad spectrum detector configured to collect photons and acquire intensity measurements for different frequencies at each sample time. The backscatter imaging system further comprises a mechanism configured to move the emitter and the broad spectrum detector in helical motion along a medium being imaged while the emitter emits substantially monochromatic radiation to the medium and the broad spectrum detector collects photons backscattered from the medium and acquires a set of pluralities of intensity measurements. The intensity measurement in each plurality of intensity measurements is associated with a different frequency. The backscatter imaging system further comprises one or more processors configured to transform the set of pluralities of intensity measurements into three-dimensional image data of the medium. In one aspect, the backscatter imaging system further comprises a mounting element and a stop (e.g., a lead bar and a lead stop). The emitter and the broad spectrum detector are mounted to opposing ends on one side of the mounting element. The stop is located on the one side of the mounting element, between the emitter and the broad spectrum detector. In this aspect, the mechanism is configured to rotate and translate the mounting member to move the emitter and the broad spectrum detector in helical motion.

According to one aspect, the one or more processors use an inverse transform for a Modified Cormack Circular Arc Transform based on helical motion to transform the set of pluralities of intensity measurements into three-dimensional image data of the medium. According to other aspects, other inversion methods may be used to transform the set of pluralities of intensity measurements into three-dimensional image data.

Certain aspects pertain to an backscatter imaging method comprising moving an emitter and a broad spectrum detector in helical motion along a medium being imaged, emitting substantially monochromatic radiation to the medium by the emitter in helical motion, collecting photons backscattered by the medium and acquiring a set of pluralities of intensity measurements using the broad spectrum detector in helical motion, wherein the intensity measurement in each plurality of intensity measurements is associated with a different frequency, and transforming the set of pluralities of intensity measurements into three-dimensional image data of the medium. In one aspect, the emitter and the broad spectrum detector are moved in the helical motion by translating and rotating a mounting element upon which the emitter and the broad spectrum detector are mounted to opposing ends on one side. In one example, the method further comprises substantially blocking radiation directly from the emitter to the broad spectrum detector using lead stop located between the emitter and the broad spectrum detector.

These and other features are described in more detail below with reference to the associated drawings.

DETAILED DESCRIPTION

Figure 1:
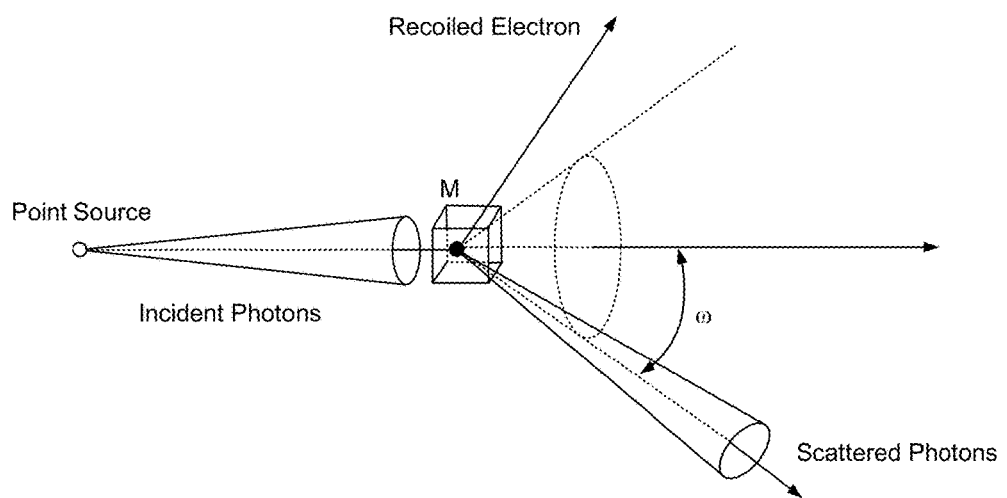
FIG. 1 is a schematic illustration of Compton scattering of photons from a point source.

Certain embodiments will be described below with reference to the accompanying drawings. The following description is directed to certain implementations for the purposes of describing various aspects of this disclosure. However, a person having ordinary skill in the art would readily recognize that the teachings herein can be applied in a multitude of different ways. Thus, the teachings are not intended to be limited to the implementations depicted solely in the Figures, but instead have wide applicability as will be readily apparent to one having ordinary skill in the art. Moreover, although the backscatter imaging systems and methods are described herein as implemented with X-rays, it would be understood to those skilled in the art that these systems and methods can be used with, or with minor modification accommodate, gamma rays and other high energy radiation by simply selecting different detector designs with sensitivity at the desired radiation modality. The choice of implemented radiation source/detector will be influenced by the typical material to be imaged, intervening material to "see through" before the imaged volume is reached, and available source/detector hardware technology given the volume, power, and temperature constraints specific to the intended application.

Embodiments described herein are generally directed to backscatter imaging methods and systems for three-dimensional imaging of density variations of a medium. A backscatter imaging system generally comprises an emitter/detector assembly with a substantially monochromatic, substantially non-collimated, X-ray emitter and a broad spectrum x-ray detector capable of measuring the energy spectrum of x-rays backscattered by a nearby medium. In some aspects, the emitter/detector assembly typically includes a mounting element (e.g., bar or rod) upon which the X-ray emitter and X-ray detector are affixed at opposing ends. The emitter/detector assembly also includes an X-ray blocking/absorbing stop (also referred to herein as a "shield" or a "block") between the X-ray emitter and the X-ray detector. This stop is designed to substantially block/absorb X-rays from direct, non-scattered propagation between the emitter and the detector. The backscatter imaging system further comprises a mechanism assembly configured to translate and rotate the emitter/detector assembly so that the emitter and the detector are moved in complementary helical paths to sweep the integrated X-ray radiation path through three-dimensional space during a data acquisition operation of a backscatter imaging method, fully sampling the three-dimensional volume so encountered. After or during the data acquisition period, the backscatter imaging method employs the Compton relation and a transform, such as an inverse transform of a modified Cormack's Circular Arc Transform, to utilize the data collected by the detector to image the medium being scanned in 3-D. The backscatter imaging methods may overcome low signal-to-noise ratio by implementing repeated passes and longer integration times should the imaged material be highly absorptive or possess a small backscatter cross-section with respect to the incident radiation. Increasing the source intensity also ameliorates these concerns.

For simplicity, the backscatter imaging systems and methods of various embodiments are described herein with respect to implementing X-rays. These backscatter imaging systems and methods can also be used, additionally or alternatively, with gamma rays by using a gamma ray source, in accordance with other embodiments.

According to certain implementations, backscatter imaging techniques may have one or more technical advantages. One advantage is that a backscatter imaging system can provide one-sided imaging i.e. the emitter and the detector scan the medium from the same side. The ability for one-sided imaging is particularly useful in non-destructive inspection and identification of material composition and structure of the surrounding medium. For example, a backscatter imaging system can be used for non-destructive inspection of an oil well wall and identification of mineralogy of rock formations surrounding the oil shaft. The backscatter imaging system can three-dimensionally image the well wall from within the oil well shaft to non-destructively inspect the wall for potential defects to determine wall integrity. The emitter/detector assembly can also three-dimensionally image beyond the well wall into the surrounding area for mineralogical identification of rock formations including the detection of the saturation level of petroleum and gas in the surrounding rock formations. In certain cases, the backscatter imaging system could be considered for use while drilling. In these cases, the systems could aid in seeking oil safely and efficiently while drilling, which could increase worker safety and decrease likelihood of environmental damage. As another example, a backscatter imaging system could be used to missions on Mars, Venus, Europa, and beyond. Currently, methods of analyzing rock formations include abrading/drilling into the formations to be able to analyze the interior. Implementing a backscatter imaging system would allow a rover, lander, or balloon-carried instrument to simply near a rock formation with the backscatter imaging system and three-dimensionally image the internal material composition and structure without touching the surface. Another advantage of the backscatter imaging technique is that a single emitter and a single detector can be used in implementations, which allows for a compact design such as a hand-held imager. Such a compact design could be used to insert into an access shaft to locate trapped victims in a crisis situation. Also, compact imagers such as a hand-held implementation can be more easily used to inspect a small region such as an organ of a human body. Compact X-ray imagers are particularly useful in implementations where spatial confinement or compactness is required such as in a well shaft or in all space missions where there is a crucial need for compact equipment. Compact X-ray imagers can also be used for the nondestructive inspection of ordinary objects like water pipes and electrical conduits behind walls, the nondestructive inspection of airplane structures to detect metal fatigue or composite interlayer delamination and nondestructive inspection of other machinery. Another advantage to the proposed backscatter imaging technique is that the beam from the emitter does not need to be collimated and the detector collects X-rays from all angles which increases the signal-to-noise ratio for a given intensity of the detected X-rays. This also allows for a simplified design since (intensity-reducing) collimators and a spatial array of detectors are not needed.

I. Compton Scattering and the Modified Cormack Circular Arc Generalized Radon Transform Compton Scattering The backwards scattering of a photon by a resting electron is generally referred to as Compton scattering. When high energy X- or gamma radiation shines through a medium, the intensity of the radiation weakens as it traverses matter mainly due to Compton scattering.

FIG. 1 shows a schematic illustration of Compton scattering of photons from a point source incident on a site, M, and with a scattering angle, w. The scattering photon energy, E, corresponds to the scattering angle, ω, by the Compton relation:

$$E = E(\omega) = E_0 \frac{1}{1 - \varepsilon\cos(\omega)}, \quad \text{(Eqn. 1)}$$

Where: $E_0$ is energy of incident photons and E is ratio of $E_0$ to electron rest energy.

The differential number of particles, $d^2N_{SC}$, from a volume element, dM, and a solid angle, dΩ, along a direction making an angle ω with the incidence beam can be determined based on the differential scattering cross section, $d\sigma_C/d\Omega$, the incidence photon flux density, $\varphi_{in}$, and n(M), the electron density at the scattering site, M, in volume differential element, dM. For a given incident energy, angular distribution of scattered photons around the scattering site, M, is no longer isotropic, but depends on the energy E(ω) of the incident beam which depends on the scattering direction, ω, according to:

$$d^2N_{SC} = \varphi_n n(M) dM \pi r^2 P(\omega) d\Omega_{SC} \quad \text{(Eqn. 2)}$$

Eqn. 2 does not take into account attenuation of the intensity of the photons as they travel through the target material and beam spreading from the straight line propagation of the beam. For radiation emitted from a point source, S, and incident on site, M, as shown in FIG. 1, these effects are taken into account when evaluating the detected photon flux density. When taking these effects into account, the differential number of particles $d^2N_{SC}$ scattered in a solid angle $d\Omega_{SC}$ is provided by:

$$d^2N_{SC} = \quad \text{(Eqn. 3)}$$
$$\frac{I_0}{4\pi} m_\sigma(SM) A_{in}(SM) n(M) dM \pi r_e^2 P(\omega) A_{out}(MD) m_{\sigma'}(MD) d\Omega_{SC}$$

The attenuation factors on the traveled distances SM and MD from Eqn. 3 are given by:

$$A_{in}(SM) = \exp\left[-\int_0^{SM} ds \mu(S+sM)\right], \quad \text{(Eqns. 4a, 4b)}$$
$$A_{out}(MD) = \exp\left[-\int_0^{MD} ds \mu(S+sD)\right]$$

Here, μ(M) is the matter linear attenuation coefficient of the material at site M and the respective beam spreading factor $m_\sigma(r)$ has the form of:

$$m_\sigma(r) = \left(\frac{1}{\pi\sigma}\tan^{-1}\frac{\sigma}{2r}\right)^2 \quad \text{(Eqn. 5)}$$

Where: σ is the linear size of scattering volume and r is the distance travelled.

Eqn. 2 is, however, the fundamental equation used in the Compton scattered image problem. $N_{SC}$ represents a 3D map of the electron cloud density of the target medium from Compton Scattering. The 3D map of the electron cloud density can be used to determine an image of the internal structure of the target medium. Additional details regarding the Compton scattering of X-rays can be found in T. T. Truong and M. K. Nguyen (2012)," Recent Developments on Compton Scatter Tomography: Theory and Numerical Simulations, Numerical Simulation—From Theory to Industry," InTech, <http:/dx.doi.org/10.5772/50012> (2012), which is hereby incorporated by reference in its entirety.

Cormack Circular Arc Generalized Radon Integral Transform

When wide-angles are used for both an X-ray source and X-ray detector with a multichannel analyzer, each measured energy channel is a sum of all scattering sites located on a circular arc starting from the emitter and ending at the detector, which is generally referred to as an "isogonic line." This is the case because the energy of Compton scattering is related to the scattering angle, ω. A more detailed discussion of isogonic lines can be found in Kondic, N. N. et al., "Density field determination by an external stationary radiation source using a kernel technique, in Measurements in polyphaser flows," ASME Winter Annual Meeting, D. E. Stock Ed., pp. 37-51 (1978), which is hereby incorporated by reference for this discussion.

The term "isogonic curve" used herein generally refers to circular arcs along which the material exposed to X-ray is emitting photons at the same energy level and is based on a similar term from geomagnetism. The measured intensity of the backscattered X-ray photons at each energy channel is an integral transform of the electron density of an isogonic curve which is a circular arc in this case. This backscattered data measures summed (integral) values along the isogonic curve. To obtain the complete integral transform in 2-D, all angular rotations in the plane between the detector and the target are measured. Together, these measurements provide an integral transform of a planar section of the target medium.

By summing Eqn. 3 over the scattering sites, M, the attenuated transform of electron density, n(M), on a circular arc for fixed source, S, and fixed detector, D, can be provided as Cormack Circular Arc Integral Transform:

$$\hat{n}(\omega, \phi) = \int_{R^2} dM \frac{I_0}{4\pi} m_\sigma(SM) A_{in}(SM) \quad \text{(Eqn. 6)}$$
$$n(M) \pi r_e^2 P(\omega) A_{out}(MD) m_{\sigma'}(MD) \delta(Circ.Arc)$$

Where: δ(Circ.Arc) is the Dirac distribution concentrated on the chosen circular arc The Cormack Circular Arc Integral Transform of Eqn. 6 is invertible and the inverse transform can be used to determine an angular portion of the 2-D image slice of the target medium from the energy measurements. To generate a three-dimensional image using the Cormack Circular Arc Integral Transform requires that the inverse transform be applied after the data for each slice is collected, which introduces a time delay as well as the need for data storage. More detailed discussion of the Cormack Circular Arc Integral Transform can be found in Cormack, A. M., "Representation of a function by its line integrals, with some radiological applications," J. Appl. Phys., 34, 2722-27 (1963), Cormack, A. M., J. Appl. Phys., 35 2908-12 (1964), Cormack, A. M., "The Radon transform on a family of curves in the plane," Proc. Am. Math. Soc., 83 325-30 (1981), and Cormack, A. M., "The Radon transform on a family of curves in the plane," II Proc. Am. Math. Soc., 86 293-8 (1982).

The Modified Cormack Circular Arc Transform

The original Radon integral transform of an image described above is based on straight lines, summing the pixel values of all possible straight lines going through a two dimensional image. The Generalized Radon transform refers to integral transforms that are not based on straight lines, but based on another shape. In Cormack's Circular Arc Generalized Radon Transform implementations, the photons backscattered from a circular arc in the material were used in the imaging process. An example of an implementation that uses generalized Radon transforms for imaging with gamma rays is described in U.S. Pat. No. 5,430,787 and PCT publication WO1011059545, which are hereby incorporated by reference for the discussion of generalized Radon transforms.

According to certain aspects, backscatter imaging systems and methods discussed herein implement a modified imaging scheme based on the Cormack Circular Arc Integral Transform. Instead of imaging arcs of circles as in the original Cormack Circular Arc Integral Transform, these backscatter imaging systems use a helical path and image the arcs of the helix instead of the arcs of circles. At any instant, the backscatter imaging method is imaging an infinitesimal circular arc using the Cormack Circular Arc Integral Transform, however, the motion along the axis of the helix causes the integral (the summing of Compton-scattered photons at the same energy level) to be performed along the helical circular arc with a modified Cormack Circular Arc Transform.

The Generalized Radon Transforms discussed in the section above are a subfamily of Integral Transforms. Integral Transforms include Generalized Radon Transforms and other types of integral transforms. A first example for imaging using integral transforms is discussed for comparison to a second modality. In the first example, imaging is performed on an object one slice at a time. The imaging instrument moves in steps across a straight line in front of the object being scanned. After moving one step, the instrument stops and images a slice of the object in front of the instrument. The slice is perpendicular to the straight line of the instrument motion. To image the slice using the Cormak Circular Arc Integral Transform, the instrument needs to move in a circular arc about the straight line of the path. The second example can be distinguished from this first example. For instance, instead of imaging an arc, a partial circle, the second example can also image an entire circle. This extends imaging capability to inside a pipe such as an oil pipeline. In addition, instead of imaging across a straight line path, this second example can image across any smooth curve in three-dimensional space. If, for example, the pipe is bent or twisted, the second example would be able to follow the curved path of the bent or twisted pipe. By permitting the instrument to move in any smooth curve, a wall can also be imaged by going up and down across the wall as while the moving in a helical motion. In one case, the helical path would somewhat resemble a slinky toy with multitudes of coils along a smooth twisted curve.

Helical Motion

In the backscatter imaging systems of embodiments, both the emitter and the detector are moved along a helical path in order to achieve the helical circular arcs which can be used with the Modified Cormack Circular Arc Transform to image the medium in 3-D. Although the helical motion described in many examples herein is centered about and follows a straight line path such as a helix centered about an axis, the helical motion does not need to follow a straight line path according to other embodiments. The helical motion can be along any smooth path to image the medium to use the backscatter imaging techniques. For example, helical motion centered along a path that is a curve in two or three-dimensional space can be used. A helical motion along a curve could be used in the instance where a tube, such as an oil pipe line, is curved or bent. In this case, the backscatter imaging system can image the pipe wall and surrounding material by moving the emitter and detector assembly in a helical motion along the curved or bent path.

Figure 5:
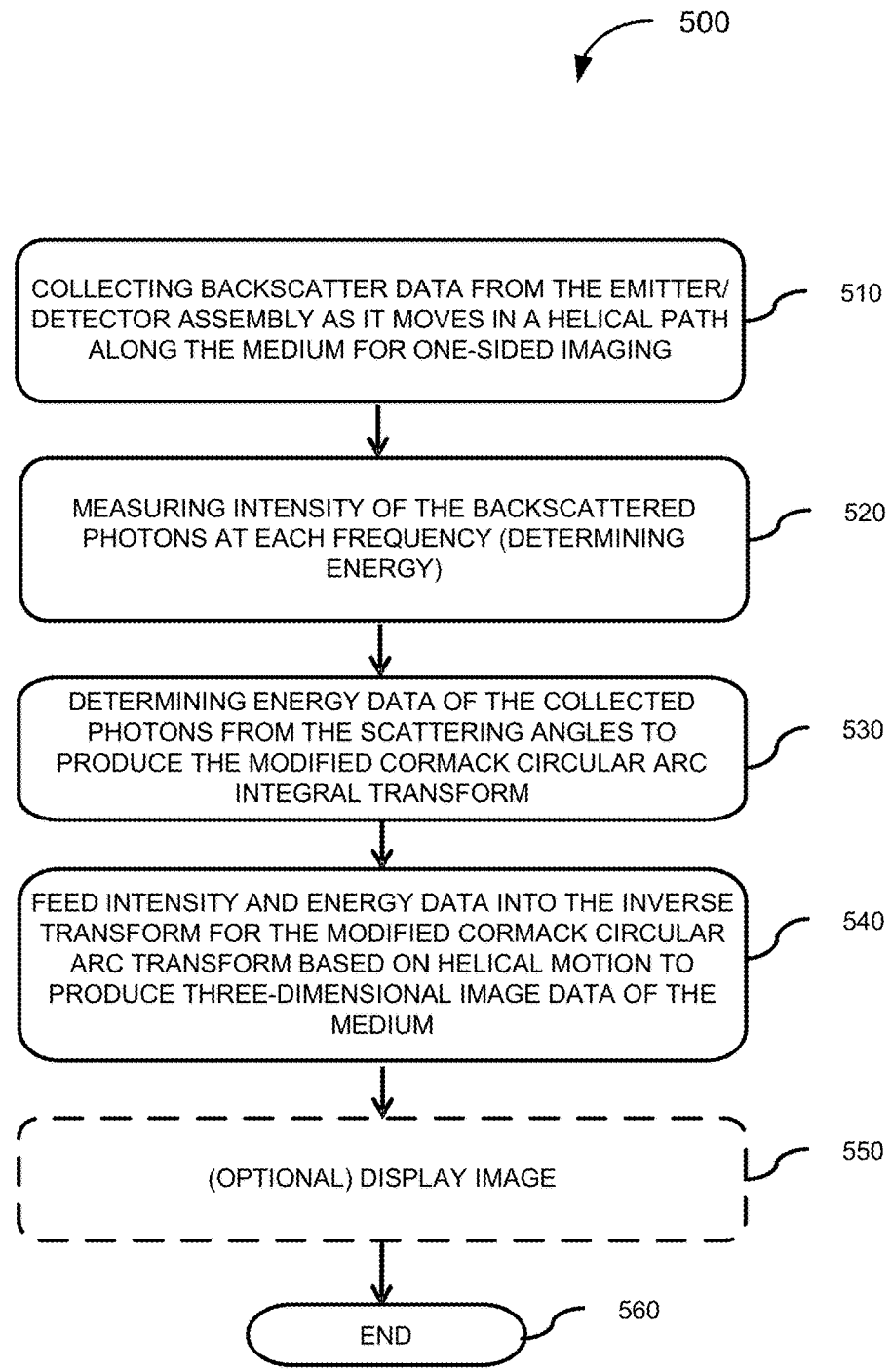
FIG. 5 is a flowchart depicting operations of a backscatter imaging method, according to various implementations.

Moreover, the backscatter imaging system can be used to image the 3-D interior behind a large area surface (e.g., a volume behind a wall) by moving the backscatter imaging system along the surface, for example, in a first direction (e.g., horizontal direction) and/or a second direction (e.g., vertical direction) orthogonal to the first direction. The surface may be, for example, of a wall of a building, a housing of machine, a compartment of a vehicle such as a truck, the delicate wings of a plane, a rock formation, and so on. As the emitter/detector assembly with the emitter coupled to the detector is slowly moved along the surface, the emitter and the detector are simultaneously moving in a helical motion in order to achieve the helical circular arcs to image the 3-D interior of the medium. In one implementation, the emitter/detector assembly with the emitter and detector is attached onto an X-Y stage or other mechanism capable of moving the assembly in the x- and/or y-direction along the surface. FIG. 5 illustrates an example of the horizontal and vertical movement of an emitter/detector assembly in front of a wall.

II. Backscatter Imaging Systems

Figure 2:
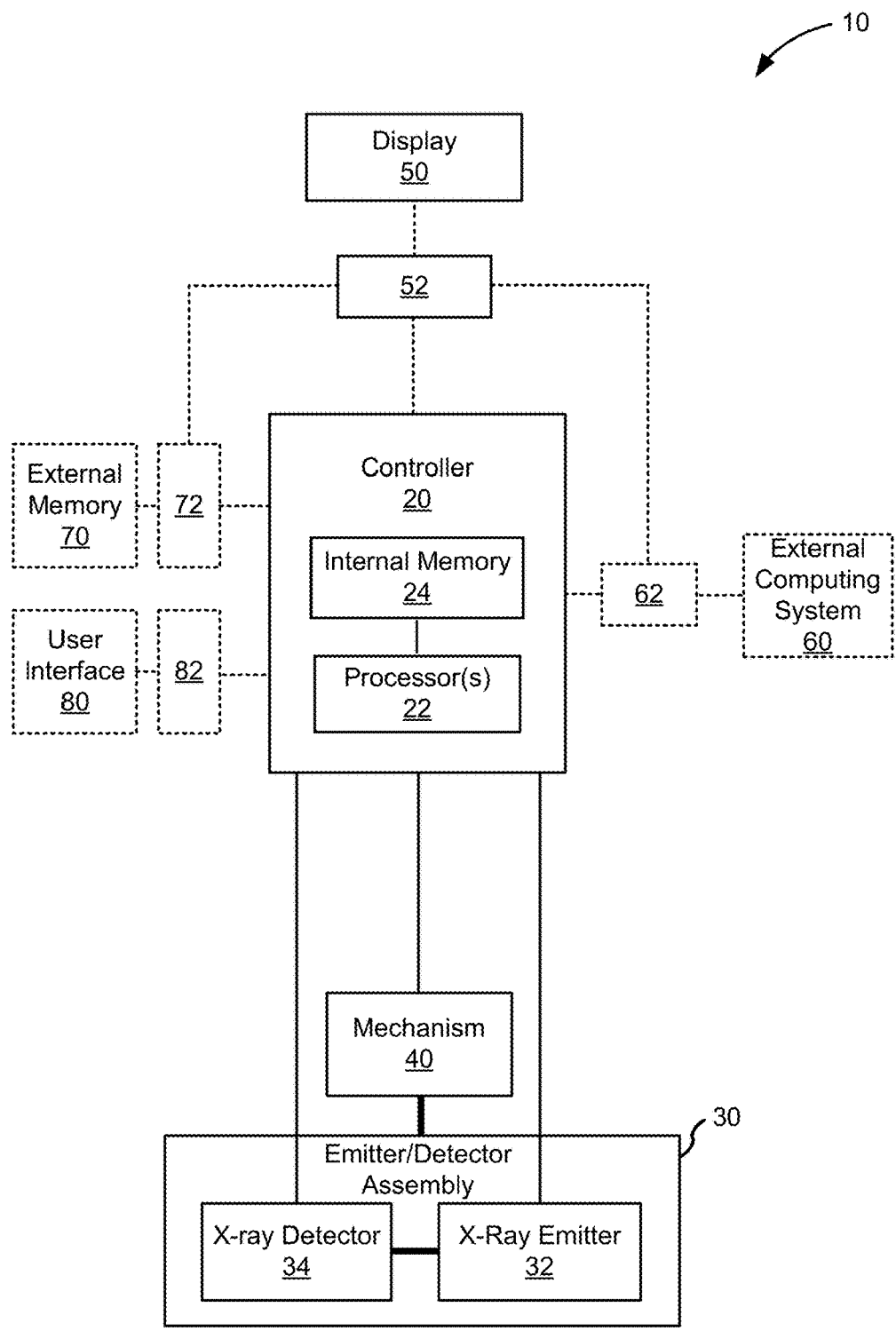
FIG. 2 illustrates a simplified block diagram of a backscatter imaging system, in accordance with various implementations.

FIG. 2 illustrates a simplified block diagram of a backscatter imaging system 10, according to various implementations. The backscatter imaging system 10 comprises a controller 20 with one or more processors 22 and an internal memory 24 in electrical communication with the one or more processors 22. The backscatter imaging system 10 further comprises an assembly 30 with an X-ray emitter 32 and an X-ray detector 34 coupled together also referred to herein as the "emitter/detector pair." During operation, the assembly 30 with the X-ray emitter 32 and an X-ray detector 34 is located to one side of a medium being scanned for three-dimensional imaging. The backscatter imaging system 10 further comprises a mechanism 40 coupled to the assembly 30 and configured to rotate and translate the assembly 20 to move the X-ray emitter 32 and the X-ray detector 34 in complementary helical paths also referred to herein as "helical motion." At a high level, the backscatter imaging system 10 is configured or configurable to move the X-ray emitter 32 and the X-ray detector 34 in helical motion to sweep the integrated X-ray radiation path through the medium while sampling intensity measurements of backscattered photons to generate signals in different spectral bins, and to process the signals in the spectral bins using an inverse transform, for example, of a Modified Cormack Circular Arc Transform (other transform methods are possible) to generate three-dimensional image (imaged volume) data of the medium that corresponds to variations in density or other properties of the scanned medium. Each of the spectral bins is associated with a sum of all scattering sites along an isogonic curve. As discussed above, an isogonic curve refers to circular arcs along which the material exposed to X-ray is emitting photons at the same energy level.

The X-ray emitter 32 is designed to emit high intensity, substantially monochromatic and un-collimated X-rays. The X-ray emitter 32 includes a source of high intensity, substantially monochromatic X-rays. The use of high intensity, substantially monochromatic X-rays allows for the application of the Compton relation in Eqn. 1 that tightly ties the scattering angle of photons to X-ray energy. The X-ray emitter 32 is in electrical communication with the controller 20 to receive power and/or control signals from the controller 20 to control (e.g., stop/start) emission of the monochromatic, non-collimated X-rays during operation.

The X-ray detector 34 is a wide angle, broad spectrum detector designed to measure the intensity of photons in different spectral bins within the full spectrum of incoming back-scattered X-rays from the medium. As mentioned above, each of the spectral bins is associated with a sum of all scattering sites along an isogonic curve and each isogonic curve refers to the circular arcs along which the material exposed to X-ray is emitting photons at the same energy level. The X-ray detector 34 is designed to receive incoming X-rays from a wide solid angle, which may help increase the signal-to-noise ratio of the backscatter imaging system 10. The X-ray detector 34 is configured or configurable to record intensity measurements at sample times during the data acquisition phase of the backscatter imaging method. The X-ray detector 34 is in electrical communication with the controller 20 to receive power and/or control signals from the controller 20 to control the taking of measurements and for communication of signal(s) with data readings taken by the X-ray detector 34 to the controller 20. In one example, the controller 20 sends control signals to both the X-ray emitter 32 and the X-ray detector 34 to synchronize the X-ray emissions with the exposure time of the X-ray detector 34.

In certain implementations, the assembly 30 further comprises a mounting element that is a bar, rod, or other shape made of a material that substantially blocks/absorbs X-rays such as lead. In these cases, the X-ray detector 34 and the X-ray emitter 32 are coupled together by mounting them to the mounting element, for example, facing substantially the same orientation. In some cases, the assembly may also include a stop of material located between the X-ray detector 34 and the X-ray emitter 32 to prevent direct stimulation. The stop is made of a material that can substantially block/absorb X-rays emitted from the X-ray emitter 32 such as lead.

The mechanism 40 is in electrical communication with the controller 20 to receive power and/or control signals from the controller 20 to control the movement of the assembly 30 such that the X-ray detector emitter 32 and the X-ray detector 34 are moved along complementary helical paths to sweep the integrated X-ray radiation path through three-dimensional space, fully sampling a volume in 3-D.

The one or more processor(s) 22 of the controller 20 and, additionally or alternatively, other processor(s) of the backscatter imaging system 10 (e.g., a processor of the external computing system 60) execute instructions stored on a computer readable memory (e.g., the internal memory 24 or external memory 70) to perform the operations of the backscatter imaging system 10. For example, one or more processor(s) 22 of the controller 20 control the emission of X-rays from the X-ray emitter 32 and the timing of the measurements (e.g., the exposure times of the detector for a particular measurement) taken by the X-ray detector 34 during the data acquisition phase. The one or more processor(s) 22 of the controller 20 may also control the mechanism 40 to cause the movement of the X-ray emitter 32 and the X-ray detector along complimentary helical paths. One or more processors of the backscatter imaging system 10 also perform operations of the XIB method to process the intensity measurements of different spectral bins to determine a three-dimensional image of variations in density of material in the scanned medium using a Modified Cormack Circular Arc Transform or another transform.

Although certain embodiments of the backscattered systems and/or methods are described herein as using a Modified Cormack Circular Arc Transform, another transform can be used according to another embodiment.

The backscatter imaging system 10 optionally (denoted by dashed line) further includes a communication interface 52 and a display 50 in communication with the communication interface 52. The controller 20 is configured or configurable to output raw data, processed data such as image data, and/or other data over the communication interface 52 for display on the display 50. The backscatter imaging system 10 also optionally includes a communication interface 62 and an external computing device 60 in communication with the communication interface 62. The backscatter imaging system 10 also optionally includes a communication interface 72 and an external memory device 70 in communication with the communication interface 72 for optional storage of data to the external memory device 422. The backscatter imaging system 10 also optional includes a communication interface 82 in communication with a user interface 80 for receiving input from an operator of the system 10. The user interface 80 is in electrical communication with the controller 20 through the communication interface 82 to be able to send a control signal to the controller 20 based on input received at the user interface.

Each of the communication interfaces 52, 62, 72, and 82 is in electrical communication with the controller 20. The described electrical communication between components of the backscatter imaging system 10 may be able to provide power and/or communicate data. The electrical communication between components of the backscatter imaging system 10 described herein may be in wired form and/or wireless form.

Although not shown, the assembly 30 or another system component may further comprises a GPS module and associated logic included in computer readable memory of the backscatter imaging system 10 for determining the location of the assembly 30. This location information can be used to determine the relative location of three-dimensional image with respect to the geographical location. For example, the location information used to correlates the three-dimensional image to a particular longitude and latitude. Additionally or alternatively, one or more components of the backscatter imaging system 10 may comprise a power source for powering one or more system components.

In FIG. 1, the controller 20 is in communication with the communication interface 52 which is in communication with the display 50. In certain implementations, the controller 20 is configured or configurable by a user (also referred to herein as an "operator") to output raw data or processed data over the communication interface 52 for display on the display 50. In some implementations, the controller 20 also can be configured or configurable to output raw data as well as processed data (for example, after image processing) over a communication interface 62 to an external computing system 60. Indeed, in some implementations, one or more of the backscatter imaging operations can be performed by such an external computing system 60. In some implementations, the controller 140 also can be configured or configurable by a user to output raw data as well as processed data over a communication interface 72 for storage in an external memory device 70.

In some implementations, the backscatter imaging system 10 further includes one or more additional interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the various system components can be electrically coupled to communicate with the controller 20 over one or more of a variety of suitable interfaces and cables such as, for example, USB interfaces and cables, ribbon cables, Ethernet cables, among other suitable interfaces and cables.

According to certain implementations, the backscatter imaging system comprises an emitter/detector assembly that is in a compact form. For example, a single X-ray emitter and a single X-ray detector may be affixed to a mounting element, such as a lead bar, sized with a width large enough to affix the X-ray emitter and single X-ray detector to opposing ends. In these implementations, the backscatter imaging system also includes a mechanism configured to rotate and translate the mounting element in order to move the X-ray emitter and the X-ray detector in a helical motion (i.e., in complementary helical paths) centered about a line or a curve. In one example, the mechanism may be attached to a flexible rod that can flex around a curve such as a curved pipe. In this case, the flexible rod is coupled to the mounting element so that the mechanism can translate the X-ray detector/emitter pair around the curve while they rotate in a helical motion.

According to various embodiments, the X-ray emitter and X-ray detector assembly is designed to prevent the X-ray emitter from directly irradiating the X-ray detector, e.g., with a lead stop between the emitter and detector, in order to prevent stray, uninformative signals from flooding the backscattered signal regardless of geometry.

According to various implementations, the X-ray emitter and the X-ray detector are affixed in particular orientations on the emitter/detector assembly. For example, the X-ray emitter is in a first orientation forming a first angle between the first orientation and a line at a reference plane (e.g., plane of the surface of the rotating bar shown in FIGS. 3A and 4A) and the X– detector is in a second orientation forming a second angle between the second orientation and the line at the reference plane. For example, in FIGS. 3A and 4A, the X-ray emitter and X-ray detector are each affixed at a 90 degree orientation from a plane at a surface of the rotating bar onto which the detector and emitter are affixed. In other embodiments, the X-ray emitter and X-ray detector may have other orientations such as acute angles. For example, the X-ray emitter may be in a first orientation forming a first acute angle between the first orientation and a line at a reference plane and the X– detector may be in a second orientation forming a second acute angle between the second orientation and the line at the reference plane. Decreasing the first and second acute angles between the X-ray emitter and X-ray detector can generate higher resolution in the resulting images but reduces the penetration depth of the imaged volume.

In various implementations, the X-ray emitter, also referred to herein as an "X-ray source emitter," or simply as an "emitter," is configured to emit high intensity, substantially monochromatic and substantially non-collimated X-rays. The use of high intensity, substantially monochromatic X-rays more directly corresponds to the Compton relation in Eqn. 1 that tightly ties the scattering angle of photons to X-ray energy. The X-ray emitter includes an X-ray source of high intensity, substantially monochromatic X-rays. The optimal energy for emitted photons is influenced by several considerations. Any intervening material (instrument casing or uninteresting material surrounding the volume to be imaged) may possess more or less transparent energy windows that should be harnessed to maximize source intensity. The imaged material will have X-ray absorptivity as a function of photon energy and atomic Z-number, where the photoelectric effect absorbs rather than scatters a photon and reduces the backscatter signal. Finally, coherent Rayleigh scattering competes with the desired Compton scattering process at energies less than 10 keV reducing backscatter cross-section. Thus, the source energy utilized should be tuned to the application. In one implementation, for a low-density target with low penetration and few intervening absorbers, the X-ray emitter is designed to emit high-intensity X-rays with photon energies in the range of about 5 to about 10 keV. For high-density targets or high-penetration goals including seeing into/through rock or metal, the X-rays may have maximum energies of 300 keV, 450 keV, or higher with steadily increasing penetrative power into the medium. At 10 MeV and above, other nucleus-based material interactions could strongly compete with the desired Compton process and reduce/contaminate the imaging return signal. The system is generally agnostic to the X-ray emitter details so long as it is compact, relatively monochromatic, and evenly illuminates a broad angular region. In addition to an X-ray source, the X-ray emitter may further comprise other components. For example, the X-ray emitter may include a filter separate from or part of the X-ray source for passing X-rays of the desired wavelength and blocking/absorbing other wavelength.

In various embodiments, the X-ray emitter is designed to provide substantially non-collimated X-rays. It would be understood that the X-ray emissions from the X-ray emitter are coarsely collimated by the geometry of the system. Only the coarsest collimation of the emitter beam is used, generally provided by the absorptive mounting geometry/element, a shield to prevent direct detector illumination, and the top and bottom of any rotating housing to enforce planar emission. By using substantially non-collimated X-rays, the signal-to-noise ratio for a given intensity may be increased. In one implementation, the X-ray emitter is designed to provide X-rays spread at an angle of about 180°. Smaller angles may be selected to increase the imaged resolution near the emitter/detector pair but reduce the penetrative depth of images volume. In one implementation, the X-ray emitter is designed to provide X-rays spread at an angle of about 90°. The distance between the top and bottom surfaces of the housing defines the axial "width" of the emitted beam and defines the z-axis resolution obtained, where a larger distance increases emitter intensity, but lowers imaged resolution. This engineering parameter will be defined based on the emitter intensity used, the Compton backscatter coefficient of the medium being imaged, and the desired resolution in the axial dimension.

In various implementations, the X-ray detector, also referred to herein as "detector," refers to a broad spectrum detector designed to measure the intensity of photons in different spectral bins within the full spectrum of incoming back-scattered X-rays from the medium. The X-ray detector is refined in its spectral (energy) resolution, measuring the full spectra of incoming back-scattered x-rays. Each of the spectral bins is associated with a sum of all scattering sites along an isogonic curve of the scanned medium. These detectors are commonly available in the field of energy dispersive X-ray spectroscopy, where they are used to determine material composition rather than spatially image. The spectral bin size (delta frequency per bin) directly maps to the desired spatial resolution of the final volume image in the radial and angular dimension. Smaller bins provide finer spatial resolution, while more numerous bins provide increased imaged volume. This is coupled to the actual X-ray penetration into the target medium defined by the source intensity and photon energy used, as spectral bins sensitive to strongly down-shifted backscatter photons require that such photons statistically survive the associated deep penetrative path. The X-ray detector is also designed to receive incident X-ray radiation from a wide angle, and in some cases, from all angles. In various implementations, the X-ray detector is designed to receive photons within an angle within a range of about 45 degrees to 180 degrees. In one implementation, the X-ray detector is designed to receive photons within an angle of about 180 degrees. In a more closed in implementation, the X-ray detector is designed to receive photons within an angle of about 45 degrees. Various types of commercially available X-ray detectors are suitable for use in a backscatter imaging system of certain implementations. For example, a low-resolution, inexpensive imaging system might favor the use of the XR-100CR Si-PIN X-Ray Detector made by Amptek®, which is located in Bedford, Mass., USA. Whereas a higher resolution, science-grade imaging system would prefer the use of the Fast SDD Ultra-high Performance Silicon Drift Detector made by the same company. The X-ray detector includes a multichannel analyzer for measuring energy channels associated with the different frequencies within the range of frequencies measured by the broad spectrum detector. Each measured energy channel is generally the sum of all scattering sites located on a circular arc (i.e. isogonic curve) starting from the emitter and ending at the detector.

It would be understood to those skilled in the art that although the backscatter imaging system of various implementations is designed so that the X-ray emitter primarily receives X-ray backscattered from the scanned medium being imaged, a relatively small amount of stray light may be also received. These stray X-rays are reduced or eliminated through standard optical system design including the block between the emitter and detector, but residual leakage always remains due to reflection from system components in even the finest designs. The backscatter imaging methods described herein assume these stray X-rays are of sufficiently low signal so as not to obscure the imaging signal.

In various implementations, the X-ray detector is configured or configurable to record, over time, intensity measurements in different spectral bins during a data acquisition phase. Each intensity measurement is acquired over an exposure time. Over the course of the data acquisition phase, the X-ray detector acquires a sequence of intensity measurements while the X-ray emitter is emitting substantially monochromatic, substantially non-collimated X-rays.

The degree to which the medium attenuates the intensity of the X-ray radiation depends on the density and other physical characteristics of the medium. The material composition and structure of the medium can be determined based on the spectrum of the X-rays scattered by the medium and measured by an X-ray detector. According to the Compton relation shown in Eqn. 1, the angle of the X-ray scattering angle is proportional to incident photon energy. Given that the X-ray emitter is a monochromic source, each intensity measurement of the received spectrum can be directly mapped to the angle at which the photon must have scattered. Each spectral bin is an integrated measurement of all photons that scattered at a given angle. The set of scattering points corresponding to a single angle forms the isogonic curve for that given angle, a circular arc joining the X-ray emitter and the X-ray detector defined by the precise scattering angle required to have been emitted from the source and reach the X-ray detector. The counts (measurements) in the spectral bins, therefore, are the input to the modified Cormack's Circular Arc Radon Transform inverting isogenic curves into voxels of a three-dimensional imaged volume of the medium. Moreover, there is a modulation of the backscattered signal that relates to the material composition of the imaged volume. While this is the desired signal in energy dispersive X-ray spectroscopy, this may be considered a distortion term in the backscatter imaging system that could artificially "darken" or "make insensitive" certain imaged voxels for a given geometry. By rotating the detector/emitter assembly, however, each spatial voxel is imaged at multiple Compton energies, providing an unambiguous imaged region. In one aspect, additional operations may be used to perform volumetric compositional analysis of the imaged volume to generate a hyperspectral image.

In various implementations, the backscatter imaging system includes a mounting element, also referred to herein as a "backing," upon which the X-ray emitter and the X-ray detector are affixed at opposing ends and in most cases, to the same surface. In one implementation, one or both of the X-ray emitter and the X-ray detector are located at or near the edges at the opposing ends of the mounting element. When the mounting element is rotated and translated so that its center of rotation moves along a line or curve, the X-ray emitter and X-ray detector assembly follows helical motion about the line or curve. The X-ray emitter and X-ray detector pair are moved in a helical motion in achieve the helical circular arcs required for using with the Modified Cormack Circular Arc Transform to image the medium in 3-D. Although many of the illustrated examples describe the mounting element as a bar, other shapes can be used such as a rod, cylinder, a disc, etc. In most cases, the X-ray emitter and the X-ray detector are located to have the same orientation (i.e. facing the same direction). The X-ray emitter and the X-ray detector are affixed to the mounting element by any method that would be suitable for maintaining the integrity of the X-ray emitter and the X-ray detector. For example, the X-ray emitter and the X-ray detector may be affixed with an adhesive. Alternatively, soldering or another method may be used. Generally, the mounting element is sized with a width at least as wide as the width of the X-ray detector and the X-ray emitter. In one implementation, the mounting element is made of a material that substantially blocks X-rays such as lead. In this case, the mounting element blocks X-rays so that the non-collimated X-rays from the X-ray emitter are spread in a direction away from mounting element.

In various implementations, a small stop is placed between the emitter and detector to prevent direct stimulation. The stop is made of a material that substantially blocks/absorbs X-rays emitted from the X-ray emitter. The stop is sized to have a height sufficient to block the direct X-rays from the X-ray emitter. In one example, the stop has a height that is or just above the height of the emitter and/or the detector.

In various implementations, the backscatter imaging system includes a mechanism assembly with a mechanism configured to translate and rotate the mounting element with the emitter/detector pair affixed thereon so that the emitter and the detector are moved in complementary helical paths to sweep the integrated X-ray radiation path through three-dimensional space, fully sampling the volume in 3-D so encountered. The mechanism assembly may include a rod or other linking member coupling the mechanism to the mounting element. Generally, the linking member will be attached at or near the center of gravity of the mounting element.

According to various implementations, the backscatter imaging system includes one or more processors such as one or more processors of a controller and/or of an external computing system. The one or more processors execute instructions stored in memory, internal and/or external, to perform the functions of the backscatter imaging system. Some of the functions performed by the processor(s) include: 1) controlling the movement of the emitter/detector assembly, 2) controlling emissions from the X-ray emitter, and 3) controlling the sampling by the X-ray detector. The one or more processors may also perform operations for transforming the intensity measurements of the photons received at the detector into three-dimensional image data and/or converting the three-dimensional image data into display data. In certain cases, the one or more processors execute instructions stored in memory, internal and/or external, and send signals to system components to control their functions. For example, the controller may be in electrical communication with the mechanism to control rotation/translation of the X-ray detector and the X-ray emitter to have helical motion. In some cases, the one or more processors receive signal(s) from the X-ray detector with intensity measurements during the data acquisition period.

In various implementations, the X-ray detector provides digital output encoding a plurality of separate signals, one signal for each bin. The number of signals in the plurality may be in the thousands according to one aspect. Although generally the X-ray detector of various embodiments provides digital output, in another implementation, the X-ray detector provides an analog signal and the backscatter imaging system includes an analog-to-digital (A/D) converter configured to convert the analog signal into a digital signal.

During the data acquisition period, the backscatter imaging system scans the nearby medium by translating the assembly with the emitter and detector along a line or a curve as the emitter and the detector are in helical motion. In some implementations, the backscatter imaging system may scan over a large surface area by slowly moving the assembly with the detector and emitter across the surface. For example, a hand-held implementation may be moved slowly in a zig zag pattern across a large surface area. In one implementation, the backscatter imaging system scans the nearby medium a single time during the data acquisition phase. In another implementation, the backscatter imaging system scans the nearby medium multiple times (e.g., 2, 3, or 4 times) during the data acquisition phase.

During the data acquisition phase, the emitter/detector assembly is slowly spun in a helical motion. Although a single turn of the rotating assembly may not provide measurements that can be used to generate a three-dimensional image of the medium, repeated measurements accomplished by slowly spinning the emitter and detector assembly acquires sufficient independent measurements to allow the Modified Cormack Circular Arc Transform to be used to determine three-dimensional image data of the medium.

In certain implementations, the backscatter imaging method will include an adjustment phase before data acquisition during which a speed of rotation and translation of the emitter/detector assembly that will be used during the data acquisition phase will be determined and/or the system components may be calibrated. During this adjustment phase, a speed and translation will be determined that is based on one or more of the intensity of the X-ray emissions, the volume of material to be imaged, the X-ray detector efficiency among other characteristics of the system implemented. In one implantation, the speed of rotation/translation is determined that will allow for multiple reads for each rotational angle of the emitter/detector. The overlapping passes of the forming helix may improve resolution and/or signal-noise-ratio of the results. In addition or alternatively, multiple passes (e.g., up, then down, then up as shown in FIG. 5) will also provide overlapping passes. In this example, the backscatter imaging system requires a positional component such as a GPS module configured to determine with high fidelity, the positional coordinates of the emitter/detector assembly in order to overlap the grids of the resulting data.

Some examples of backscatter imaging systems are shown in FIGS. 3A, 3B, 4A, 4B, and 5. Some of these backscatter imaging systems have one or more components that are similar to those of the backscatter imaging system 10 in FIG. 1 above.

Configuration A

Figure 3A:
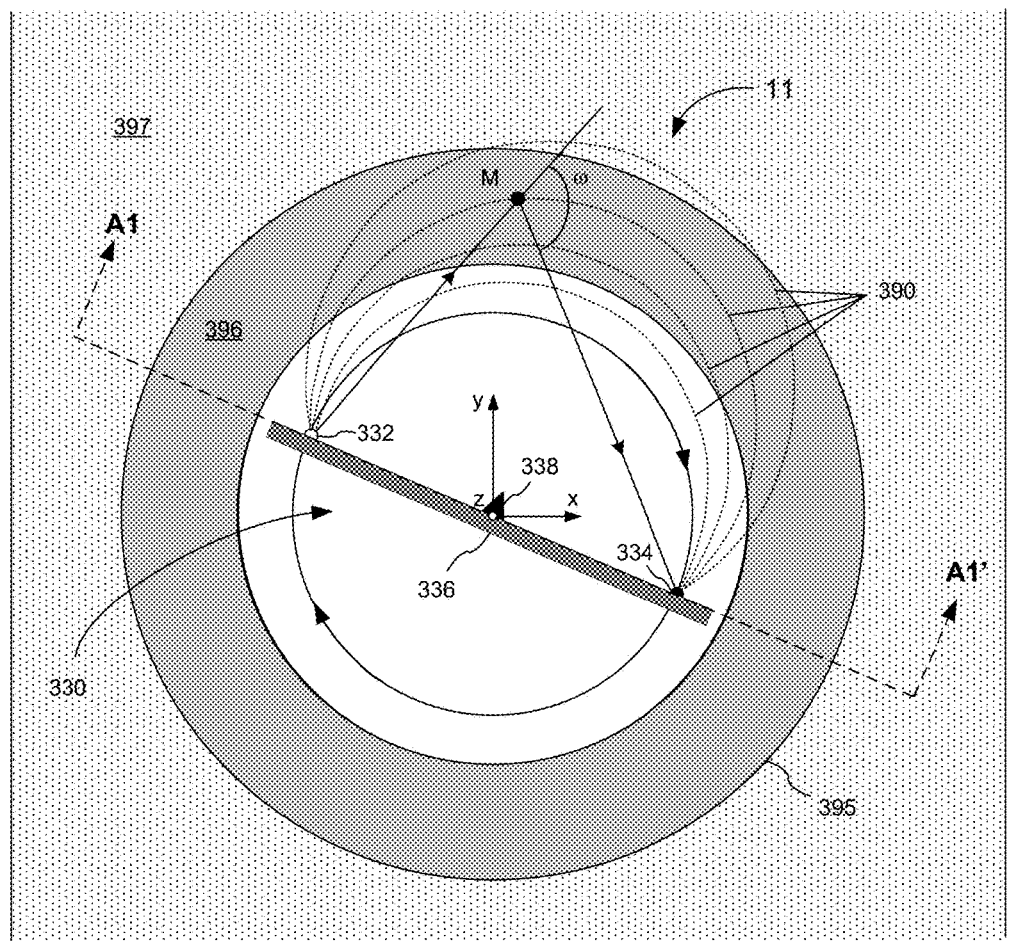
FIG. 3A is a schematic drawing of a cross-sectional view of a portion of a backscatter imaging system introduced into a pipe for acquiring three-dimensional image data of the pipe wall and/or the surrounding exterior medium, according to certain implementations.
Figure 3A:
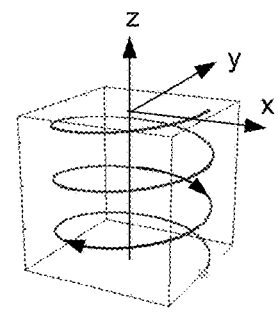
Figure 3B:
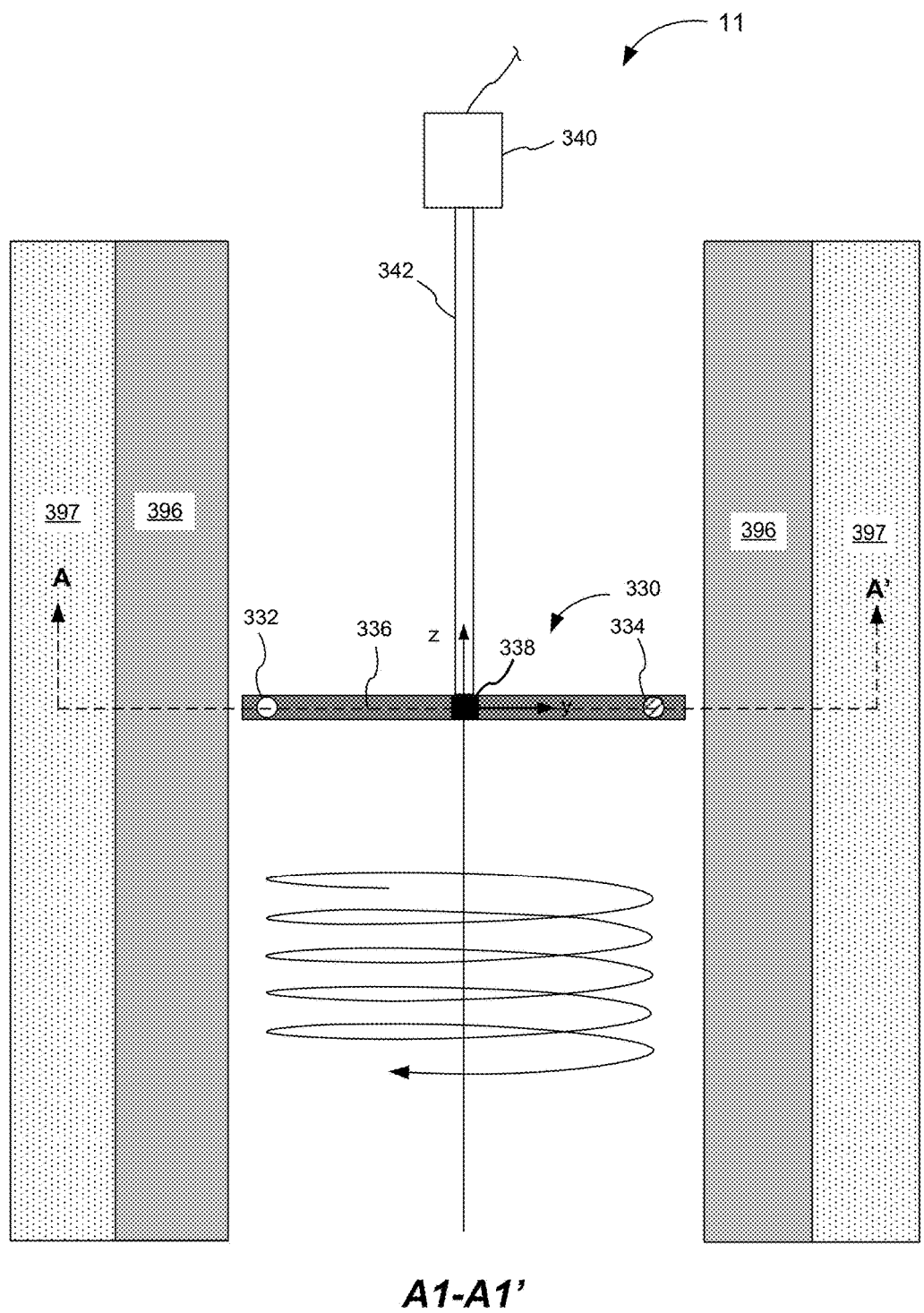
FIG. 3B is a schematic drawing of another cross-sectional view of a portion of the backscatter imaging system in FIG. 3A.

FIG. 3A is a schematic drawing of a cross-sectional view A-A' of a portion of a backscatter imaging system 11 introduced into a pipe 395 for acquiring three-dimensional image data of density variations in the pipe wall and/or the surrounding exterior medium, according to certain implementations. FIG. 3B is a schematic drawing of another cross-sectional view A1-A1' of a portion of the backscatter imaging system 11 shown in FIG. 3A. In these illustrated examples, the backscatter imaging system 11 scans the wall 396 of the pipe 395 and a depth into the surrounding exterior medium 397. The surrounding exterior medium 397 may be, for example, rock formations or objects outside the wall of the pipe. In one example, the backscatter imaging system 11 is introduced to a pipe in a building or an access duct of a mine in a crisis situation. It would be understood to those skilled in the art that the depth of imaging is related to the properties of the medium being imaged and the intensity of the X-ray emissions.

The backscatter imaging system 11 includes an emitter/detector assembly 330 comprising an X-ray emitter 332, an X-ray detector 334, a mounting element 336 in the form of a bar (e.g., lead bar) having a constant cross section, and a lead stop 338 affixed to the mounting element 336 between the X-ray detector 334 and the X-ray emitter 332 to prevent direct stimulation from X-rays emitted from the X-ray emitter 332. The lead stop 338 is shown as a triangle, but other shapes may be used. The X-ray emitter 332 and the X-ray detector 334 are affixed to one side and at opposing ends of the mounting element 336 and in the same orientation normal to the side facing surface of the mounting element 336.

As shown in FIG. 3B, the backscatter imaging system 11 further comprises a mechanism 340 for translating and rotating the emitter/detector assembly 330. The mechanism 340 is coupled to the emitter/detector assembly 330 by a rod 342. In one implementation, the rod 342 is a flexible rod.

Although not shown, the backscatter imaging system 11 further comprises a controller with one or more processors, internal/external memory, optionally a display, and various connectors (for communication and/or power) between the components of the backscatter imaging system 11. The illustrated example shows a connector (communication/power) at one end in electrical communication with the mechanism 340. The other end of the connector is in electrical communication with a processor(s) of the controller or an external computing system. The one or more processors executes instructions a stored in memory, internal and/or external, to perform the functions of the backscatter imaging system 11. Some of the functions performed by the processor(s) include: 1) controlling the movement of the emitter/detector assembly 330, 2) controlling emissions from the X-ray emitter 332, and 3) controlling the sampling by the X-ray detector 334. The one or more processors may also perform operations for transforming the intensity measurements of the photons received at the detector into three-dimensional image data and/or converting the three-dimensional image data into display data. In certain cases, the one or more processors execute instructions stored in memory, internal and/or external, and send signals to system components to control their functions. For example, the controller may be in electrical communication with the mechanism to control rotation/translation of the X-ray detector 434 and the X-ray emitter 432 to have helical motion. In some cases, the one or more processors receive signal(s) from the X-ray detector 434 with intensity measurements during the data acquisition period.

The backscatter imaging system 11 also includes an x-axis, a y-axis, and a z-axis. The x-axis and y-axis lie in a plane at the surface of the mounting element 336. The z-axis is orthogonal to this plane. The X-ray emitter 332 and the X-ray detector 334 are affixed (e.g., with adhesive, soldering, etc.) to one side and at opposing ends of the mounting element 340. The X-ray emitter 332 and X-ray detector 334 have the same orientation perpendicular to a plane at a side surface of the mounting element 340. Although the X-ray emitter 320 and the X-ray detector 330 in this illustration are shown located at the same distance from the z-axis, it would be understood that the distance from the z-axis may be adjusted based on the mass of balancing the masses of the X-ray emitter 320 and the X-ray detector 330.

The X-ray emitter 332 is configured to emit high intensity, substantially monochromatic and substantially non-collimated X-rays. In one implementation, the X-ray emitter 332 can emit high-intensity X-rays with photon energies in the range of about 5 to about 10 keV. In one implementation, the X-ray emitter 332 is configured to emit high-intensity X-rays have maximum energies of, for example, greater than 300 keV, greater than 450 keV, or higher. In one implementation, the X-ray emitter is designed to provide X-rays spread at an angle of about 180°.

The X-ray detector 334 is a broad spectrum detector that is refined in its spectral (energy) resolution, measuring the full spectra of incoming back-scattered x-rays from the X-ray emitter 332. Each of the spectral bins is associated with a sum of all scattering sites along an isogonic curve of the scanned medium. The X-ray detector 334 is also designed to receive incident X-ray radiation from a wide angle, and in some cases, from all angles in front of the mounting element 340, which can be made of a material that blocks/absorbs X-rays. In some implementations, the X-ray detector 334 is designed to receive photons within an angle within a range of about 45 degrees to 180 degrees. In one implementation, the X-ray detector 334 is designed to receive photons within an angle of about 180 degrees. In one implementation, the X-ray detector 334 is designed to receive photons within an angle of about 45 degrees. The X-ray detector includes a multichannel analyzer for measuring energy channels associated with the different frequencies within the range of frequencies measured by the broad spectrum detector.

In FIGS. 3A and 3B, the backscatter imaging system 11 is shown at an instant during the data acquisition phase. At this instant, X-rays are being emitted from X-ray emitter 320 and X-ray detector 330 is measuring incoming X-rays backscattered from the medium. To schematically illustrate an instance of Compton scattering, in FIG. 3A an arrow representing a single photon is shown incident a scattering site, M, in the wall 396 and a photon scattered at an scattering angle, ω is represented by another arrow For illustration purposes, four isogonic curves are shown between the X-ray emitter 320 and X-ray detector 330.

Although the backscatter imaging system 11 is illustrated as moving the emitter/detector assembly 330 in a straight line along the z-axis, it would be understood that the backscatter imaging system 11 could be used to move along a curved path according to one aspect. For example, the backscatter imaging system 11 could implement a rod 342 that is flexible and flex the rod 342 to move the emitter/detector assembly 330 around a curve. In this example and other implementations, the backscatter imaging system 11 may also include a protective casing, also referred to herein as a "housing," around at least the emitter/detector assembly 330.

During the data acquisition phase, the backscatter imaging system 11 translates the mounting element 336 along the z-axis while rotating the mounting element 336 to move the X-ray emitter 332 and the X-ray detector 334 in helical motion. The arrows along the circle through the X-ray emitter 332 and the X-ray detector 334 show the direction of the rotation. The schematic representation at the bottom right illustration of FIG. 3A shows an example of the helical path followed by the emitter/detector. In this illustrated example, the helical motion is about the straight line along the z-axis. Although the helical motion is shown in a clockwise direction, it would be understood that, in addition or alternatively, a counter clockwise direction can also be used. During the data acquisition phase, the emitter and detector are slowly spun in a helical motion. The speed of rotation and translation of the emitter/detector is determined based on one or more of the intensity of the X-ray emissions, the volume of material to be imaged, the X-ray detector efficiency among other characteristics of the system implemented. In one implantation, the speed of rotation/translation is determined that will allow for multiple reads for each rotational angle of the emitter/detector. In addition or alternatively, multiple scans of the medium can be implemented during the data acquisition phase which also provides overlapping passes. In one implementation, the backscatter imaging system further comprise a positional component such as a GPS module configured to determine positional coordinates of the emitter/detector assembly during rotation/translation in order to overlap the grids of the resulting data from overlapping passes.

Configuration B

In certain implementations, a backscatter imaging system is moved in front of a surface of a medium to acquire three-dimensional image data of the medium behind the surface. In one example, such as backscatter imaging system is moved slowly across a large area surface, for example, in a pattern such as a zig zag pattern. In these implementations, the backscatter imaging system may be designed in a compact form such as a hand-held design that is moved slowly across the surface by an operator. In another example, the compact backscatter imaging system may be mounted to an x-y stage that slowly moves the backscatter imaging system or a portion thereof (e.g., emitter/detector assembly) across the surface. The medium may be scanned once or multiple times during the data acquisition phase.

Figure 4A:
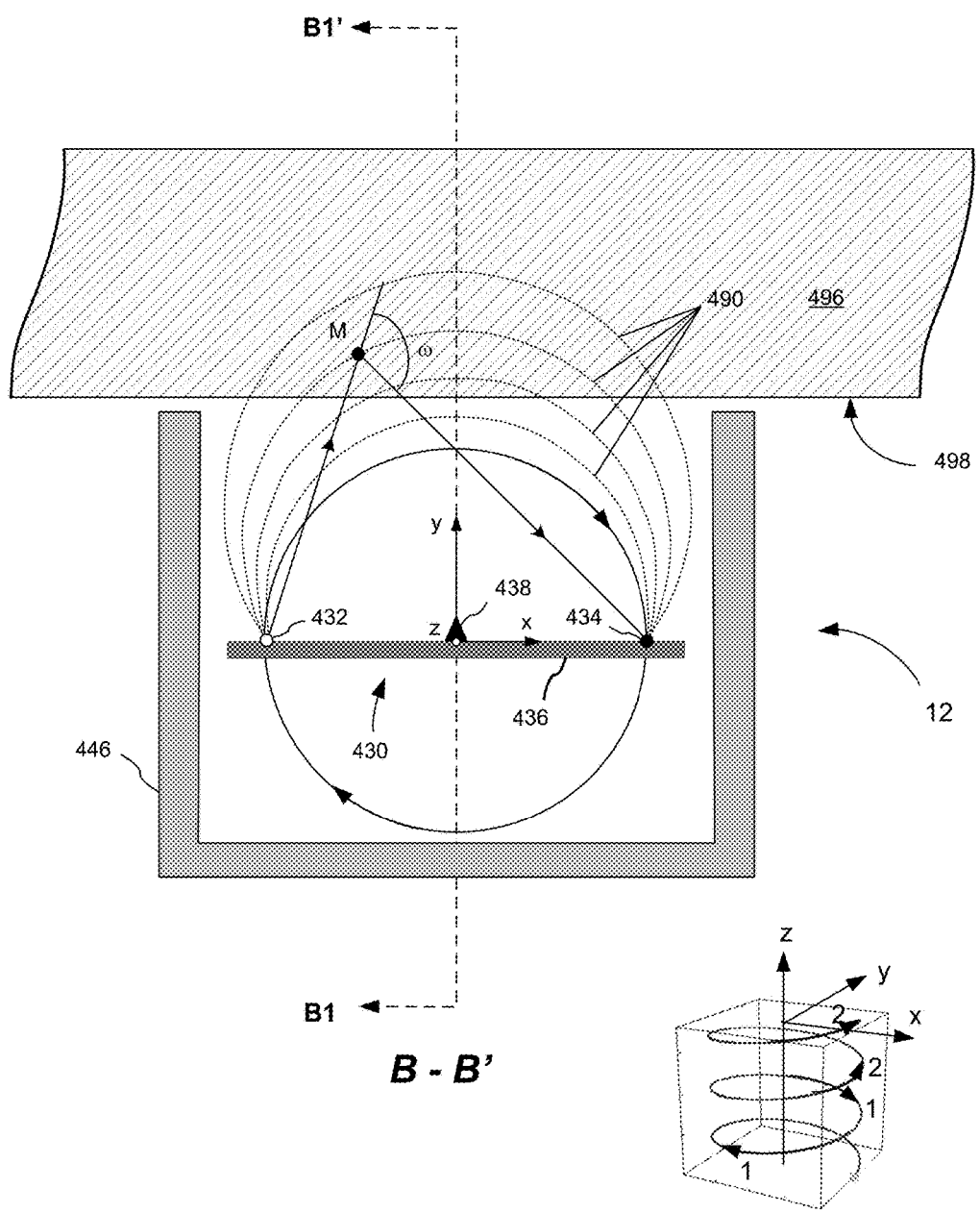
FIG. 4A is a schematic drawing of a cross-sectional view of a portion of a backscatter imaging system in front of a surface of a medium being imaged, according to certain implementations.
Figure 4B:
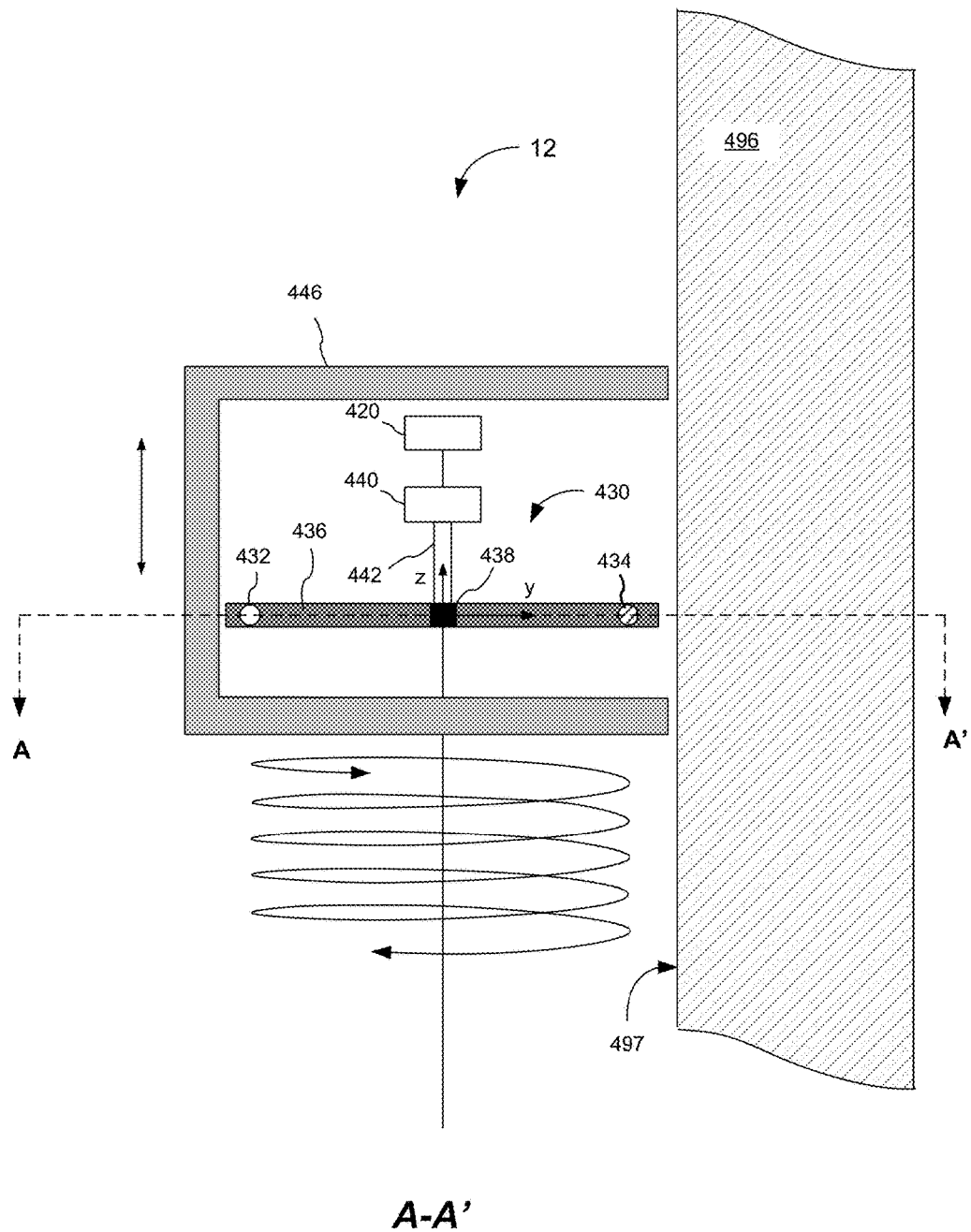
FIG. 4B is a schematic drawing of another cross-sectional view of a portion of the backscatter imaging system in FIG. 4A.
Figure 4C:
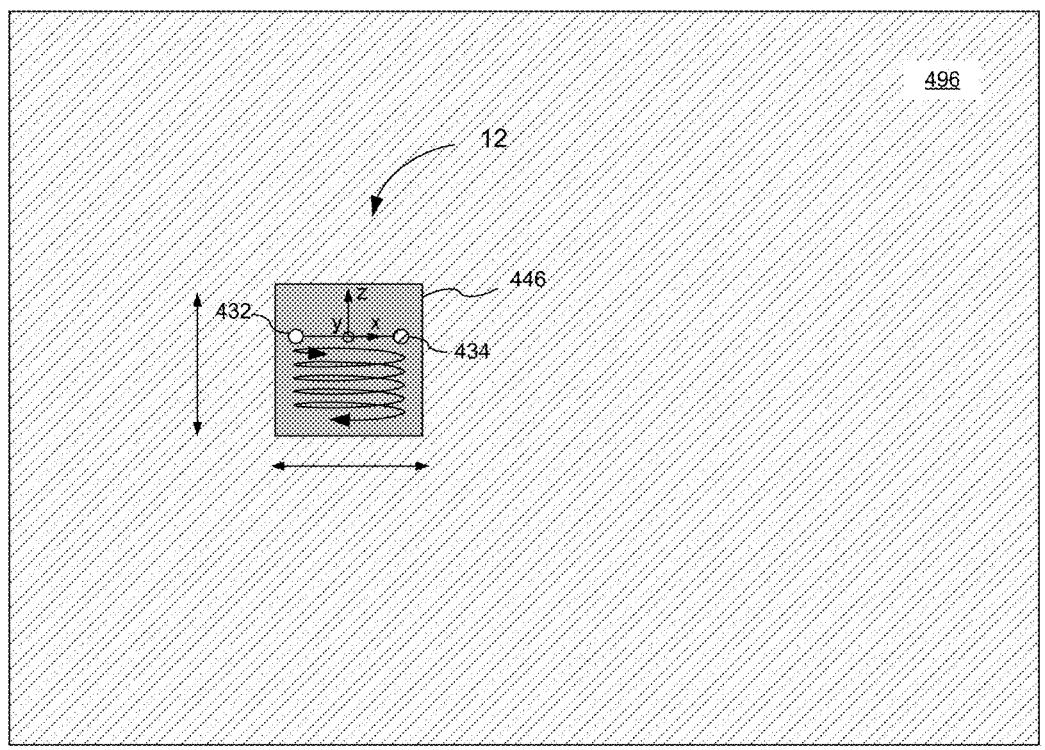
FIG. 4C is a schematic drawing of a front view of a portion of the backscatter imaging system in FIGS. 4A and 4B.

FIG. 4A is a schematic drawing of a cross-sectional view B-B' of a portion of a backscatter imaging system 12 in front of a surface 497 of a medium 496, according to certain implementations. In these implementations, the medium is a long wall, for example, of a building, a vehicle, a rock formation, etc. FIG. 4B is a schematic drawing of another cross-sectional view B1-B1' of the backscatter imaging system 12 shown in FIG. 4A. FIG. 4C is a schematic drawing of a front view of a portion of the emitter/detector assembly 12 shown in FIGS. 4A and 4B. FIG. 4C shows the backscatter imaging system 12 during operation being moved in a horizontal and/or vertical direction across the surface 497 to scan into the medium 496 behind the surface 497 to acquire three-dimensional image data of density variations through the medium 496 being scanned. Although a planar surface is shown, a surface with curvature can also be imaged with backscatter imaging system 12.

As shown in FIG. 4B, the backscatter imaging system 12 includes an emitter/detector assembly 430 comprising an X-ray emitter 432, an X-ray detector 434, a mounting element 436 in the form of a bar (e.g., lead bar) having a constant cross section, and a lead stop 438 affixed to the mounting element 436 between the X-ray detector 434 and the X-ray emitter 432 to prevent direct stimulation from X-rays emitted from the X-ray emitter 432. The lead stop 438 is shown as a triangle, but other shapes may be used. The X-ray emitter 432 and the X-ray detector 434 are affixed to one side and at opposing ends of the mounting element 436 and in the same orientation normal to the side facing surface of the mounting element 436.

As shown in FIG. 4B, the backscatter imaging system 12 further comprises a mechanism 440 for translating and rotating the emitter/detector assembly 430. The backscatter imaging system 12 further comprises a controller 420 with one or more processors. The controller 420 is in electrical communication with the mechanism 440. The backscatter imaging system 12 further comprises a rod 442 coupled to the mechanism 440 on one end and to the center of the mounting element 436 on the other end. The mechanism 440 is configured to translate and rotate the detector/emitter assembly 430. The backscatter imaging system 12 further comprises a housing 446 with an enclosure within which reside the detector/emitter assembly 430, the controller 420, the mechanism 440, and the rod 442. In one implementation, the housing 446 is made of material that blocks X-rays such as lead. The housing 446 includes an opening on one side between the inner surfaces of the top and bottom walls of the housing 446. During operation, the backscatter imaging system 12 is positioned so that the opening faces the medium being imaged. The distance between the inner surfaces of the top and bottom walls of the housing 446 define the axial "width" of the emitted beam.

Although not shown, the backscatter imaging system 11 further comprises internal/external memory, optionally a display, and various connectors (for communication and/or power) between the components of the backscatter imaging system 12.

The one or more processors of the controller 420 and/or of an external computing system execute instructions stored in memory, internal and/or external, to perform the functions of the backscatter imaging system 12. Some of the functions performed by the processor(s) include: 1) controlling the movement of the emitter/detector assembly 430, 2) controlling emissions from the X-ray emitter 432, and 3) controlling the sampling by the X-ray detector 434. The one or more processors may also perform operations for transforming the intensity measurements of the photons received at the detector into three-dimensional image data and/or converting the three-dimensional image data into display data. In certain cases, the one or more processors execute instructions stored in memory, internal and/or external, and send signals to system components to control their functions. For example, the controller may be in electrical communication with the mechanism to control rotation/translation of the X-ray detector 434 and the X-ray emitter 432 to have helical motion. In some cases, the one or more processors receive signal(s) from the X-ray detector 434 with intensity measurements during the data acquisition period.

The backscatter imaging system 12 also includes an x-axis, a y-axis, and a z-axis. The x-axis and y-axis lie in a plane at the surface of the mounting element 436. The z-axis is orthogonal to this plane. The X-ray emitter 432 and the X-ray detector 434 are affixed (e.g., with adhesive, soldering, etc.) to one side and at opposing ends of the mounting element 440. The X-ray emitter 432 and X-ray detector 434 have the same orientation perpendicular to a plane at a side surface of the mounting element 440. Although the X-ray emitter 420 and the X-ray detector 430 in this illustration are shown located at the same distance from the z-axis, it would be understood that the distance from the z-axis may be adjusted based on the mass of balancing the masses of the X-ray emitter 420 and the X-ray detector 430.

The X-ray emitter 432 is configured to emit high intensity, substantially monochromatic and substantially non-collimated X-rays. In one implementation, the X-ray emitter 432 is configured to emit high-intensity X-rays with photon energies in the range of about 5 to about 10 keV. In one implementation, the X-ray emitter 432 is configured to emit high-intensity X-rays have maximum energies of, for example, greater than 300 keV, greater than 450 keV, or higher. In one implementation, the X-ray emitter is designed to provide X-rays spread at an angle of about 180°.

The X-ray detector 434 is a broad spectrum detector that is refined in its spectral (energy) resolution, measuring the full spectra of incoming back-scattered x-rays from the X-ray emitter 432. Each of the spectral bins is associated with a sum of all scattering sites along an isogonic curve of the scanned medium. The X-ray detector 434 is also designed to receive incident X-ray radiation from a wide angle, and in some cases, from all angles in front of the mounting element 440, which can be made of a material that blocks/absorbs X-rays. In some implementations, the X-ray detector 434 is designed to receive photons within an angle within a range of about 45 degrees to 180 degrees. In one implementation, the X-ray detector 434 is designed to receive photons within an angle of about 180 degrees. In one implementation, the X-ray detector 434 is designed to receive photons within an angle of about 45 degrees. The X-ray detector 434 includes a multichannel analyzer for measuring energy channels associated with the different frequencies within the range of frequencies measured by the broad spectrum detector.

In FIGS. 4A, 4B, and 4C, the backscatter imaging system 12 is shown at an instant during the data acquisition phase. At this instant, X-rays are being emitted from X-ray emitter 420 and X-ray detector 430 is measuring incoming X-rays backscattered from the medium. To schematically illustrate an instance of Compton scattering, in FIG. 4A an arrow representing a single photon is shown incident a scattering site, M, in the medium 496 and a photon scattered at an scattering angle, ω is represented by another arrow. For illustration purposes, four isogonic curves are shown between the X-ray emitter 420 and X-ray detector 430.

During the data acquisition phase, the backscatter imaging system 12 translates the mounting element 436 along the z-axis within the housing 446 while rotating the mounting element 436 to move the X-ray emitter 432 and the X-ray detector 434 in helical motion. At the same time, the housing 446 of the backscatter imaging system 12 is slowly moved in a horizontal direction and/or in a vertical direction across the surface 497 of the medium 496 as schematically shown in FIG. 4C. The schematic representation at the bottom right illustration of FIG. 4A shows an example of a helical path first in a clockwise direction and then in a counterclockwise direction. In another example, the helical motion may be one of a clockwise or counterclockwise direction. During the data acquisition phase, the emitter and detector are slowly spun in a helical motion. The speed of rotation and translation of the emitter/detector is determined based on one or more of the intensity of the X-ray emissions, the volume of material to be imaged, the X-ray detector efficiency among other characteristics of the system implemented. In one implantation, the speed of rotation/translation is determined that will allow for multiple reads for each rotational angle of the emitter/detector. In addition or alternatively, multiple scans of the medium can be implemented during the data acquisition phase which also provides overlapping passes. In one implementation, the backscatter imaging system further comprise a positional component such as a GPS module configured to determine positional coordinates of the emitter/detector assembly during rotation/translation in order to overlap the grids of the resulting data from overlapping passes.

III. Exemplary Backscatter Imaging Methods

Conventional methods of X-ray imaging using the original Cormack Circular Arc Integral Transform are based on imaging circles and scanning along a series of planes. For example, the detector would be moved to different positions along a straight line and at each position, stop, and image an entire circle. Then, the detector would be moved a small distance to the next position along the straight line, and image the next circle. In this way, the original Cormack Circular Arc Integral Transform was used to build up the transform of the image in 3D.

In certain embodiments, backscatter imaging methods use a modified Cormack Circular Arc Transform for imaging along a helical path sweeping through three-dimensional space. The backscatter imaging systems move the detector and the emitter in helical motion (complementary helical paths) near the medium to be imaged. At each sampling time, the detector is detecting photon energy associated with the Compton backscattered electrons along an infinitesimal circular arc. In the backscatter imaging methods, the infinitesimal circular arcs are helical in nature with the helical motion of the emitter/detector pair along a line/curve central to the helix and thus, the modified Cormack Circular Arc Transform is utilized to image the medium in 3-D. Since this Modified Cormack Circular Arc Transform can used to image based on helical motion around a curved path, the emitter/detector pair can be easily maneuvered to image a vast number of complex-shaped mediums such as a curved pipe that makes a bend of 30 degrees, 45 degrees, 90 degrees, etc. Moreover, the backscatter imaging systems and methods can be used to image a volume behind a large-area surface such as a long wall, for example, by moving emitter/detector pair to different positions in a pattern over the surface. For example, the housing around the emitter/detector assembly may be moved slowly in horizontal and/or vertical directions along the surface while the emitter/detector pair move in helical motion within the housing. Although these methods are described as using a modified Cormack Circular Arc Transform, another transform may be used according to another embodiment.

In various implementations, the backscatter imaging methods generally comprise: 1) a data acquisition phase during which the emitter/detector pair scan the medium being imaged acquiring intensity measurements over time from collected backscattered photons; 2) a three-dimensional image construction phase that determines the three-dimensional image based on the intensity measurements; and 3) an optional display phase.

In Compton scattering, an X-ray is scattered by an electron and the scattered photons suffer energy loss. As shown in Eqn. 1, the scattering angle ω is a function of the ratio of energies between incident and scattered photons. During the data acquisition the emitter/detector pair are scanned a helical motion along a line/curve along the medium being imaged to sample intensity measurements over time. The X-ray detector is a broad spectrum detector that detects X-rays for multiple spectral bins where each bin is associated with a frequency or a small range of frequencies. Each measurement in a spectral bin is output in a signal by the X-ray detector. The detection of X-rays in each spectral bin corresponds to the scattering location on one isogonic curve of a circular path between the emitter and the detector. Each measurement of a spectral bin is an integrated measurement of all photons that scattered at a given angle. This set of scattering points corresponding to a single angle forms the isogonic curve for that given angle, a circular arc joining the emitter and detector defined by the precise scattering angle required to have been emitted from the source and reach the detector. Therefore, the measurements in the different spectral bins taken as the emitter/detector assembly moves in the helical motion can be used as input to the modified Cormack Circular Arc Transform inverting differential arcs taken along the helical path into a three-dimensional image.

During the three-dimensional image construction phase, the intensity measurements are processed into three-dimensional image data. The degree to which the scanned medium attenuates the intensity of X-ray radiation depends on the density and other physical characteristics of the medium. The three-dimensional image data corresponds to variations of density in the material of the scanned medium.

During the last optional display phase, the raw three-dimensional image data or processed data may be displayed on a display such as the display 50 shown in FIG. 2. During this phase, the three-dimensional image data may be processed to generate a three-dimensional display image or a series of two-dimensional cross-sectional display images that have shading or colors (e.g., red may designate a deposit of a particular mineral in the medium) that identify particular densities or other physical characteristics in the medium.

FIG. 5 is a flowchart depicting operations of backscatter imaging methods that can be implemented by various backscatter imaging systems described herein such as those describe with respect to FIGS. 2, 3A, 3B, 4A, 4B, and 4C. In these implementations, operations 510 and 520 can be performed simultaneously as part of a data acquisition phase. Operations 530 and 540 may be performed simultaneously or in the sequence as part of a three-dimensional image construction phase. Optional operation 550 is part of a display phase, which may be performed simultaneously to or after the data acquisition phase and three-dimensional image construction phase. In one aspect, one or more of the operations 530, 540, and 550 may be after, in some cases after a time delay, operations 510 and/or 520. Although these operations are described below as using an inverse transform of a modified Cormack Circular Arc Transform, another transform may be used according to another embodiment.

At 510, the emitter and detector are moved in helical motion along a medium while the emitter provides high intensity, substantially monochromatic X-rays and the detector collects backscatter data based on X-rays backscattered from the irradiated medium. The emitter and detector are located on the same side of the medium at each position of the helical path for one-sided imaging. For example, the detector and emitter may be moved in helical motion within a pipe to image the pipe wall and/or medium surrounding the pipe. In this case, the emitter and detector are located to the same side to the inside of the pipe during helical motion. In another example, the emitter and detector may be used to image a wall where the emitter and detector are both moved along the same outside surface of the wall. In implementations of a compact form of the backscatter imaging system, the detector/emitter assembly can be moved within a compact housing while the housing is slowly moved along a large surface being imaged, for example, in a pattern across a large area surface.

In one embodiment, the emitter and detector may be moved in a helical path along a medium over multiple passes of the medium. The multiple passes may be implemented by a slow speed of translation of a compact system, for example, across a wall, by repeating the helical motion, or by positioning the emitter and detector assembly at the same location at different sample times.

In one embodiment, the X-ray emitter and/or X-ray detector receives control signals from one or more processors (e.g., of a controller or of an external computing system) to control the X-ray emissions and the sampling times for taking intensity measurements. For example, the processor(s) may send control signals to both the X-ray emitter and X-ray detector to synchronize the X-ray emissions with the exposure time of the X-ray detector.

At 520, the X-ray detector measures (samples) intensity of incoming photons at each frequency corresponding to energy. The X-ray detector is generally a wide angle, broad spectrum detector designed to measure, at each sample time, the intensity of scattered photons at each frequency within the full spectrum of back-scattered X-rays from the medium. As the emitted/detector assembly is moved in the helical motion along the medium in 510, the X-ray detector collects backscattered photons from the irradiated medium and measures an intensity of the incoming photons for each frequency in a plurality of spectral bins. The intensity measurements are acquired over time. Generally, a plurality of intensity measurements is taken at each sample time of a sequence of sample time. During data acquisition, a set of pluralities of intensity measurements is acquired where the intensity measurement of each plurality of intensity measurements is associated with a frequency/energy. At each sample time, the intensity measurement at each frequency is associated with a sum of all scattering sites along an isogonic curve (the circular arcs along which the material exposed to X-ray is emitting photons at the same energy level). For each sample time, the X-ray detector measures a plurality of intensity measurements in different spectral bins (frequencies) and outputs a signal for each bin/frequency. The signals are output from the X-ray detector and communicated to one or more processors of the imaging system.

At 530, one or more processors determine energy data from the scattering angles to produce the Modified Cormack Circular Arc Integral transform. Given that the X-ray emitter is a monochromic source, each intensity measurement of the received spectrum can be directly mapped to an angle at which the photon must have scattered based on the Compton relation in Eqn. 1. At each sample time, the signal for each spectral bin is associated with a scattering angle. In 530, the plurality of intensity measurements at each sample time is converted into energy data based on the Compton relation to produce the Modified Cormack Circular Arc Integral transform.

At 540, one or more processors feed the intensity measurements and the energy data into the inverse transform for the Modified Cormack Circular Arc Integral transform based on helical motion to produce the three-dimensional data of the medium. The degree to which the medium attenuates the intensity of the X-rays depends on the density and other physical characteristics of the medium. Hence, the material composition and structure of the medium can be determined based on the spectrum of the X-rays scattered by the medium and measured by an X-ray detector. Given that the X-ray emitter is a monochromic source, each intensity measurement of the received spectrum can be directly mapped to the angle at which the photon must have scattered based on the Compton relation in Eqn. 1. Each spectral bin is an integrated measurement of all photons that scattered at a given angle. The set of scattering points corresponding to a single angle forms the isogonic curve for that given angle, a circular arc joining the X-ray emitter and the X-ray detector defined by the precise scattering angle required to have been emitted from the source and reach the X-ray detector. The intensity measurements in the spectral bins, therefore, can be used as the input to the modified Cormack's Circular Arc Radon Transform inverting isogenic curves into voxels of a three-dimensional imaged volume of the medium. Moreover, there is a modulation of the backscattered signal that relates to the material composition of the imaged volume. While this is the desired signal in energy dispersive X-ray spectroscopy, this may be considered a distortion term in the backscatter imaging system that could artificially "darken" or "make insensitive" certain imaged voxels for a given geometry. By rotating the detector/emitter assembly, however, each spatial voxel is imaged at multiple Compton energies, providing an unambiguous imaged region.

At optional 540, a display may receive display data such as a three dimensional image or other data and display the data on a display such as the display 50 of backscatter imaging system 10. Then, the imaging method ends the imaging cycle (550). In one example, the display data is a three-dimensional image showing variations in density or other properties of the material in the scanned medium.

In an implementation where the backscatter imaging system is of a compact form where a computing system (e.g., controller) with a processor and computer readable medium are located within the housing, the operation 520 and 530 may occur at the same time. That is, the image can be created at the same time as data acquisition. This implementation has the added advantage of avoiding collection and transmittance of large volumes of data to a computing system located outside the housing.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

As used herein, the conjunction "or" is intended herein in the inclusive sense where appropriate unless otherwise indicated; that is, the phrase "A, B or C" is intended to include the possibilities of A, B, C, A and B, B and C, A and C and A, B and C. Additionally, a phrase referring to "at least one of" a list of items refers to any combination of those items, including single members. As an example, "at least one of: A, B, or C" is intended to cover: A, B, C, A-B, A-C, B-C, and A-B-C.

What is claimed is:

1. A backscatter imaging system for three-dimensional imaging, the system comprising:
    an emitter configured to emit substantially monochromatic radiation;
    a broad spectrum detector configured to collect photons and acquire a plurality of intensity measurements for different frequencies at each sample time;
    a mechanism configured to move the emitter and the broad spectrum detector in helical motion along a medium being imaged while the emitter emits substantially monochromatic radiation and the broad spectrum detector collects photons backscattered from the medium and acquires a set of pluralities of intensity measurements, wherein the intensity measurement in each plurality of intensity measurements is associated with a different frequency; and
    one or more processors configured to transform the set of pluralities of intensity measurements into three-dimensional image data of the medium.

2. The backscatter imaging system of claim 1, wherein the emitted substantially monochromatic radiation comprises X-rays and/or gamma rays.

3. The backscatter imaging system of claim 1, wherein the emitter is a single radiation source and the broad spectrum detector is a single detecting element.

4. The backscatter imaging system of claim 1, further comprising:
    a mounting element, wherein the emitter and the broad spectrum detector are mounted to opposing ends on one side of the mounting element, and wherein the mechanism is configured to rotate and translate the mounting member to move the emitter and the broad spectrum detector in the helical motion along the medium; and
    a stop on the one side of the mounting element and between the emitter and the broad spectrum detector.

5. The backscatter imaging system of claim 4, wherein the mounting element and the stop are made of lead.

6. The backscatter imaging system of claim 1, wherein the radiation incident the medium is substantially non-collimated.

7. The backscatter imaging system of claim 1, wherein the emitter and the broad spectrum detector have substantially the same orientation.

8. The backscatter imaging system of claim 1, wherein the broad spectrum detector is configured to receive photons within an angle of about 180 degrees.

9. The backscatter imaging system of claim 1, wherein the helical motion is about a curve.

10. The backscatter imaging system of claim 1, wherein the one or more processors are configured to use an inverse transform for a Modified Cormack Circular Arc Transform based on helical motion to transform the set of pluralities of intensity measurements into the three-dimensional image data of the medium.

11. A backscatter imaging method comprising:
    moving an emitter and a broad spectrum detector in helical motion along a medium being imaged;
    emitting substantially monochromatic radiation to the medium by the emitter while in helical motion;
    collecting photons backscattered by the medium and acquiring a set of pluralities of intensity measurements using the broad spectrum detector while in helical motion, wherein the intensity measurement in each plurality of intensity measurements is associated with a different frequency; and
    transforming the set of pluralities of intensity measurements into three-dimensional image data of the medium.

12. The backscatter imaging method of claim 11, wherein the substantially monochromatic radiation being emitted comprises X-rays and/or gamma rays.

13. The backscatter imaging method of claim 11, wherein moving the emitter and the broad spectrum detector in the helical motion comprises translating and rotating a mounting element upon which the emitter and the broad spectrum detector are mounted to opposing ends on one side.

14. The backscatter imaging method of claim 13, further comprising substantially blocking radiation from the emitter directly to the broad spectrum detector using a lead stop located on the mounting element between the emitter and the broad spectrum detector.

15. The backscatter imaging method of claim 14, wherein the mounting element is made of lead and the broad spectrum detector is configured to receive photons within an angle of about 180 degrees.

16. The backscatter imaging method of claim 11, wherein the emitter is a single radiation source and the broad spectrum detector is a single detecting element.

17. The backscatter imaging method of claim 11, wherein the helical motion is about a curve.

18. The backscatter imaging method of claim 11, further comprising translating a housing with the emitter and the broad spectrum detector across a surface of the medium while the emitter and the broad spectrum detector move in helical motion.

19. The backscatter imaging method of claim 18, wherein translated the housing comprises moving the housing in a pattern across the surface.

20. The backscatter imaging method of claim 11, wherein the emitter and the broad spectrum detector are moved in helical motion along the medium in multiple passes across a surface.

21. The backscatter imaging method of claim 11, transforming the set of pluralities of intensity measurements into three-dimensional image data of the medium comprises using an inverse transform for a Modified Cormack Circular Arc Transform based on helical motion to transform the set of pluralities of intensity measurements into the three-dimensional image data of the medium.

* * * * *